United States Patent
Liesenfelt et al.

(10) Patent No.: US 10,416,098 B2
(45) Date of Patent: Sep. 17, 2019

(54) THREE-DIMENSIONAL IMAGE RECONSTRUCTION USING TRANSMISSION AND SCATTER RADIOGRAPHY METHODS

(71) Applicant: GEORGETOWN RAIL EQUIPMENT COMPANY, Georgetown, TX (US)

(72) Inventors: Michael John Liesenfelt, Austin, TX (US); James Edward Baciak, Gainesville, FL (US); Gregory Thomas Grissom, Georgetown, TX (US)

(73) Assignee: GEORGETOWN RAIL EQUIPTMENT COMPANY, Georgetown, TX (US)

( * ) Notice: Subject to any disclaimer, the term of this patent is extended or adjusted under 35 U.S.C. 154(b) by 270 days.

(21) Appl. No.: 15/604,530

(22) Filed: May 24, 2017

(65) Prior Publication Data

US 2017/0343488 A1    Nov. 30, 2017

Related U.S. Application Data

(60) Provisional application No. 62/341,920, filed on May 26, 2016.

(51) Int. Cl.
   *G01N 23/04* (2018.01)
   *G01N 23/046* (2018.01)
   (Continued)

(52) U.S. Cl.
   CPC ......... *G01N 23/046* (2013.01); *G01N 23/203* (2013.01); *G06T 11/006* (2013.01);
   (Continued)

(58) Field of Classification Search
   None
   See application file for complete search history.

(56) References Cited

U.S. PATENT DOCUMENTS

| | | |
|---|---|---|
| 3,562,419 A | 2/1971 | Stewart |
| 3,942,000 A | 3/1976 | Dieringer |
| | (Continued) | |

FOREIGN PATENT DOCUMENTS

| | | |
|---|---|---|
| DE | 10040139 | 3/2002 |
| FR | 2674809 | 10/1992 |
| | (Continued) | |

OTHER PUBLICATIONS

Jhih-Shian Lee and Jyh-Cheng Chen; "A Single Scatter Model for X-Ray Ct Energy Spectrum Estimation and Polychromatic Reconstruction", IEEE Transactions on Medical Imaging, vol. 34, Jun. 6, 2015.

(Continued)

*Primary Examiner* — Hoon K Song
(74) *Attorney, Agent, or Firm* — Parsons Behle & Latimer

(57) ABSTRACT

A method for image reconstruction includes irradiating an object with a beam of radiation from a radiation source, measuring an attenuated portion of the beam, estimating a density of the object, determining a predicted attenuated portion of the beam using the density estimate, and iteratively adjusting the density estimate of the object. The predicted attenuated portion and the measured attenuated portion are compared to determine a signal difference. The density estimate of each portion of the object is adjusted by scaling the density estimate using the average signal differences of rays that intersect the portion of the object. The density estimate may be repeatedly adjusted until a difference between consecutive density estimates is below a selected threshold or a predetermined number of adjustments have been completed. The attenuated portion of the beam may include a scattered portion and a transmitted portion.

44 Claims, 9 Drawing Sheets

(51) Int. Cl.
*G06T 11/00* (2006.01)
*G01N 23/203* (2006.01)
*G06T 7/00* (2017.01)

(52) U.S. Cl.
CPC ............... *G01N 2223/3302* (2013.01); *G01N 2223/401* (2013.01); *G01N 2223/646* (2013.01); *G06T 7/0012* (2013.01); *G06T 2211/424* (2013.01); *G06T 2211/436* (2013.01)

(56) References Cited

U.S. PATENT DOCUMENTS

| | | |
|---|---|---|
| 4,040,738 A | 8/1977 | Wagner |
| 4,198,164 A | 4/1980 | Cantor |
| 4,265,545 A | 5/1981 | Slaker |
| 4,490,038 A | 12/1984 | Theurer et al. |
| 4,531,837 A | 7/1985 | Panetti |
| 4,554,624 A | 11/1985 | Wickham et al. |
| 4,653,316 A | 3/1987 | Fukuhara |
| 4,700,223 A | 10/1987 | Shoutaro et al. |
| 4,915,504 A | 4/1990 | Thurston |
| 4,974,168 A | 11/1990 | Marx |
| 5,199,176 A | 4/1993 | Theurer et al. |
| 5,245,855 A | 9/1993 | Burgel et al. |
| 5,487,341 A | 1/1996 | Newman et al. |
| 5,493,499 A | 2/1996 | Theurer et al. |
| 5,671,679 A | 9/1997 | Straub et al. |
| 5,721,685 A | 2/1998 | Holland et al. |
| 5,791,063 A | 8/1998 | Kesler et al. |
| 5,970,438 A | 10/1999 | Clark et al. |
| 6,025,920 A | 2/2000 | Dec |
| 6,064,428 A | 5/2000 | Trosino et al. |
| 6,243,657 B1 | 6/2001 | Tuck et al. |
| 6,347,265 B1 | 2/2002 | Bidaud |
| 6,356,299 B1 | 3/2002 | Trosino |
| 6,405,141 B1 | 6/2002 | Carr et al. |
| 6,526,352 B1 | 2/2003 | Breed et al. |
| 6,556,945 B1 * | 4/2003 | Burggraf ............... B61L 23/045 356/606 |
| 6,600,999 B2 | 7/2003 | Clark et al. |
| 6,615,648 B1 | 9/2003 | Ferguson et al. |
| 6,634,112 B2 | 10/2003 | Carr et al. |
| 6,647,891 B2 | 11/2003 | Holmes et al. |
| 6,681,160 B2 | 1/2004 | Bidaud |
| 6,768,959 B2 | 7/2004 | Ignagni |
| 6,804,621 B1 | 10/2004 | Pedanckar |
| 7,036,232 B2 | 5/2006 | Casagrande |
| 7,130,753 B2 | 10/2006 | Pedanekar |
| 7,164,476 B2 | 1/2007 | Shima et al. |
| 7,616,329 B2 | 11/2009 | Villar |
| 7,680,631 B2 | 3/2010 | Selig et al. |
| 2002/0070283 A1 | 6/2002 | Young |
| 2002/0196456 A1 | 12/2002 | Komiya et al. |
| 2003/0097235 A1 | 5/2003 | Theurer et al. |
| 2003/0140509 A1 | 7/2003 | Casagrande |
| 2003/0164053 A1 | 9/2003 | Ignagni |
| 2004/0021858 A1 | 2/2004 | Shima et al. |
| 2004/0088891 A1 | 5/2004 | Theurer |
| 2004/0122569 A1 | 6/2004 | Bidaud |
| 2004/0263624 A1 | 12/2004 | Nejikovsky et al. |
| 2005/0111009 A1 | 5/2005 | Keightley et al. |
| 2006/0017911 A1 | 1/2006 | Villar |
| 2006/0171704 A1 | 8/2006 | Bingle |
| 2007/0136029 A1 | 6/2007 | Selig et al. |
| 2007/0150130 A1 | 7/2007 | Welles |
| 2008/0304083 A1 | 12/2008 | Farritor et al. |
| 2009/0273788 A1 | 11/2009 | Nagle et al. |
| 2009/0319197 A1 | 12/2009 | Villar et al. |
| 2012/0033792 A1 * | 2/2012 | Kulik ..................... G01N 9/24 378/89 |
| 2016/0320523 A1 * | 11/2016 | Inanc ..................... G01V 5/145 |

FOREIGN PATENT DOCUMENTS

| | | |
|---|---|---|
| JP | 06322707 | 11/1994 |
| JP | 07146131 | 6/1995 |
| JP | 07294443 | 11/1995 |
| JP | 07294444 | 11/1995 |
| JP | 0924828 | 1/1997 |
| JP | 10332324 | 12/1998 |
| JP | 11172606 | 6/1999 |
| JP | 2000221146 | 8/2000 |
| JP | 2000241360 | 9/2000 |
| JP | 2002294610 | 10/2002 |
| JP | 2003074004 | 3/2003 |
| JP | 2004132881 | 4/2004 |
| RU | 2142892 | 12/1999 |
| SU | 1418105 | 8/1988 |
| WO | WO2011002534 | 1/2011 |

OTHER PUBLICATIONS

European Patent Office, International Search Report & Written Opinion, PCT Patent Application No. PCT/US2017/034454, dated May 25, 2017.

Man, et al. "An Iterative Maximum-Likelihood Polychromatic Algorithm for CT", Oct. 10, 2001.

RU Patent and Trademark Office; Decision on Grant for RU Patent Application No. 2007103331 dated Dec. 10, 2009.

International Searching Authority; International Search Report and Written Opinion for PCT Patent Application No. PCT/US2010/023991 dated Apr. 19, 2010.

European Patent Office; Supplementary European Search Report for European Patent Application No. 05767776.7 dated May 2, 2011.

PCT International Search Report and Written Opinion for corresponding PCT Patent Application No. PCT/US2010/025004 dated Apr. 22, 2010.

International Searching Authority; International Search Report and Written Opinion for PCT Patent Application No. PCT/US2010/029076 dated May 24, 2010.

US Patent and Trademark Office, Final Office Action for U.S. Appl. No. 12/465,473 dated Jul. 31, 2012.

US Patent and Trademark Office, Office Action for U.S. Appl. No. 12/465,473, dated Oct. 5, 2011.

US Patent and Trademark Office, Office Action for U.S. Appl. No. 11/172,618 dated Mar. 23, 2007.

US Patent and Trademark Office, Final Office Action for U.S. Appl. No. 11/172,618 dated Oct. 5, 2007.

US Patent and Trademark Office, Office Action for U.S. Appl. No. 11/172,618 dated Aug. 5, 2008.

US Patent and Trademark Office, Final Office Action for U.S. Appl. No. 11/172,618 dated Apr. 15, 2009.

European Patent Office; Communication Pursuant to Article 94(3) EPC issued in European Patent Application No. 05 767 776.7-1555; dated Nov. 26, 2015.

US Patent and Trademark Office; Office Action for U.S. Appl. No. 13/795,841 dated Sep. 17, 2014.

Mohamed Y. Shahin and Starr D. Kohn, "Development of a Pavement Condition Rating Procedure for Roads, Streets, and Parking Lots" (Technical Report M-268), vol. 1: Condition Rating Procedure, pp. 1-90, (Jul. 1979), U.S. Army Corps. of Engineers. Jul. 1, 1979.

Shawn Landers et al., "Development and Calibration of a Pavement Surface Performance Measure and Prediction Models for the British Columbia Pavement Management System", pp. 1-17, (2002), Transportation Association of Canada 2002 Conference, Winnipeg. Jan. 1, 2002.

Zheng Wu, "Hybrid Multi-Objective Optimization Models for Managing Pavement Assets", http://scholar.li b.vt.ed u/theses/avai lable/etd-02012008-154826/u nrestricted/Dissertation_Zheng_ETD.pdf, Doctoral Thesis, Virginia Tech, (Jan. 25, 2008). Jan. 25, 2008.

"Pavement Condition Index 101",pp. 30-32 and 42, OGRA's Milestones, vol. 9 #4, (Dec. 2009). Dec. 1, 2009.

(56) References Cited

OTHER PUBLICATIONS

Dare I Mes her, "Rail Radar Automated Track Assessment", pp. 1-10, (Dec. 11, 2010), Association of American Railways (AAR) Transportation Test Center, Pueblo, Colorado. Nov. 12, 2010.
US Patent and Trademark Office; Office Action for U.S. Appl. No. 14/599,757 dated Mar. 2, 2016.
Canadian Intellectual Property Office; Office Action for Canadian Patent Application No. 2,761,805 dated Sep. 7, 2016.
Canadian Intellectual Property Office; Office Action; Canadian Patent Application No. 3,008,893; Apr. 11, 2019.

* cited by examiner

THREE-DIMENSIONAL IMAGE RECONSTRUCTION USING TRANSMISSION AND SCATTER RADIOGRAPHY METHODS

CROSS REFERENCE TO RELATED APPLICATIONS

The present application claims the benefit of priority under 35 U.S.C. § 119 to U.S. Provisional Application No. 62/341,920, filed May 26, 2016, entitled "THREE-DIMENSIONAL IMAGE RECONSTRUCTION USING TRANSMISSION AND SCATTER RADIOGRAPHY METHODS," the disclosure of which is incorporated herein by reference in its entirety.

FIELD OF THE DISCLOSURE

The embodiments described herein relate to a system and method of using scatter and/or transmission radiography to create a three-dimensional reconstruction of an object.

BACKGROUND

Description of the Related Art

Computed tomography ("CT") scans typically are transmission-only radiography methods that rely upon mathematical reconstruction. Known methods and systems rely upon positioning an object along a central axis and rotating the scanning system about the object as the object translates. As the system rotates about the object, images are taken from different angles to provide cross-section views of the object. Accordingly, a plurality of axes of motion are used and the speeds of known systems and methods are limited. Known CT methods include radon transforms, back projection, filtered back projection, Feldkamp, and spiral CT.

Further, known transmission radiography methods rely upon measuring the amount of radiation blocked along rays through an object. Radiation that may be scattered in these systems is generally disregarded as noise. Some known scatter CT methods require moving an X-ray source to many positions, averaging the X-ray spectra, and ignoring the Compton scatter change of energy. These known methods and systems rely on mathematical reconstruction rather than a physics-based reconstruction.

SUMMARY

The present disclosure is directed to a system and method of using scatter and/or transmission radiography to create a three-dimensional reconstruction that overcomes some of the problems and disadvantages discussed above.

An embodiment of a penetrating radiation inspection system comprises at least one internal scanning subsystem and a processor configured to convert an estimated density of a portion of the object to a corrected estimated density. The at least one internal scanning subsystem has a radiation source and at least one detector. The radiation source is configured to produce a beam of radiation, the beam having a plurality of rays and is positioned to direct the beam of radiation into an object for internal inspection during relative translational motion between the at least one internal scanning subsystem and the object. The beam may be a plurality of beams. The at least one detector is positioned to at least partially measure an attenuated portion of the beam of radiation. The processor is configured to convert an estimated density of a portion of the object to a corrected estimated density by determining a predicted attenuated portion using a density estimate, comparing the predicted attenuated portion to the measured attenuated portion to determine a signal difference, adjusting the density estimate of the portion of the object by scaling the density estimate using signal differences of rays that intersect the portion of the object, and repeatedly adjusting the density estimate until a difference between consecutive density estimates is below a selected threshold or a predetermined number of adjustments have been completed.

The system may be stationary and include a travel path, wherein the object is translated through the system on the travel path. The system may include a surface scanning subsystem configured to scan a surface of the object to produce a three-dimensional surface profile of the object. The processor may be configured to initially estimate the density of the portions of the object within the boundary. The at least one internal scanning subsystem may be configured to measure the attenuated portion of the beam of radiation without rotating around the object.

The at least one internal scanning subsystem may be a plurality of internal scanning subsystems. At least two of the internal scanning subsystems may be oriented in different perspectives. The at least two of the internal scanning subsystems may be offset. The beam of radiation may comprise a plurality of energies. The beam of radiation may be a collimated fan beam, a collimated cone beam, or a collimated pencil beam. The at least one detector may be configured to integrate the energy of all of the measured attenuated portions of the beam of radiation. The at least one detector may be configured to determine energy levels of the measured attenuated portion of the beam of radiation.

The at least one detector may be at least one transmission detector, the attenuated portion of the beam may be a transmitted portion of the beam, and the predicted attenuated portion of the beam may be a predicted transmitted portion of the beam. The at least one detector may be at least one scatter detector, the attenuated portion of the beam may be a scattered portion of the beam, and the predicted attenuated portion of the beam may be a predicted scattered portion of the beam. The system may include collimators associated with the at least one scatter detector configured to limit detection of scattered portions of the beam of radiation to a field of view. The at least one detector may include at least one scatter detector and at least one transmission detector, the attenuated portion of the beam may include a scattered portion of the beam and a transmitted portion of the beam, and the predicted attenuated portion of the beam may include a predicted scattered portion of the beam and a predicted transmitted portion of the beam. The system may include a filter associated with at least one of the at least one scatter detector and at least one transmission detector. The filter may be configured to filter lower energy photons. The radiation source may be an X-ray, a gamma ray source, or a combination thereof.

An embodiment of a method for three-dimensional image reconstruction includes translating at least one of an object and a radiation source, irradiating the object with a beam of radiation from a radiation source, measuring an attenuated portion of the beam with a first detector in a first perspective, and converting an estimated density of a plurality of portions of the object to a corrected estimated density of each portion of the object using a computer system. The beam has a plurality of rays. The estimated density of a plurality of portions of the object is converted by determining a predicted attenuated portion of the beam in the first perspective using a density estimate, comparing the predicted attenuated portion in the first perspective to the measured attenuated portion in the first perspective to determine a signal difference of each ray in the first perspective, adjusting the density estimate of the portion of the object by scaling the density estimate using signal differences of rays that intersect the portion of the object, and repeatedly adjusting the density estimate until a difference between consecutive density estimates is below a selected threshold or a predetermined number of adjustments have been completed.

The method may include generating a three-dimensional density array representing the object using the corrected estimated densities of the portions of the object. The attenuated portion of the beam may be a scattered portion of the beam, the first detector may be a scatter detector, and the predicted attenuated portion of the beam may be a predicted scattered portion of the beam. The scatter detector may have a plurality of detector elements, each detector element having a field of view, and the rays that intersect the portion of the object are rays that intersect the portion of the object and are within an intersecting field of view of the detector elements. The attenuated portion of the beam may be a transmitted portion of the beam, the first detector may be a transmission detector, and the predicted attenuated portion of the beam may be a predicted transmitted portion of the beam.

The method may include irradiating the object with a second beam of radiation from a second radiation source. The second beam may have a plurality of rays. The method may include measuring an attenuated portion of the second beam with a second detector in a second perspective. The method may include determining a predicted attenuated portion of the second beam in the second perspective using a density estimate. The method may include converting the estimated density of the plurality of portions of the object to a corrected estimated density of each portion of the object using the average signal difference of all the rays in the first and second perspectives that intersect the portion of the object.

The attenuated portion of the beam may be a transmitted portion of the second beam, the first detector may be a transmission detector, and the predicted attenuated portion of the beam may be a predicted transmitted portion of the beam. The attenuated portion of the second beam may be a scattered portion of the second beam, the first detector may be a scatter detector, and the predicted attenuated portion of the second beam may be a predicted scattered portion of the second beam. The first beam and the second beam may be one beam. The second perspective may be offset from the first perspective. The radiation source and the second radiation source may be one radiation source. The beam of radiation from the radiation source may have a plurality of energies.

The method may include approximating the boundary of the object using a three-dimensional surface scan. The method may include initially estimating the density of the portions of the object within the boundary. The radiation source may not rotate around the object.

An embodiment of a method for three-dimensional image reconstruction includes obtaining a measured attenuated portion of each of at least one beam of radiation, the at least one beam having a plurality of rays, the at least one beam of radiation being from a radiation source and having been attenuated by interaction with an object and converting an estimated density of a plurality of portions of the object to a corrected estimated density of each portion of the object using a computer system. The estimated density of a plurality of portions of the object is converted by determining a predicted attenuated portion of the at least one beam using the density estimate, comparing the predicted attenuated portion to the measured attenuated portion to determine a signal difference, adjusting the density estimate of the portion of the object by scaling the density estimate using signal differences of rays that intersect the portion of the object, and repeatedly adjusting the density estimate until a difference between consecutive density estimates is below a selected threshold or a predetermined number of adjustments have been completed.

The method may include generating a three-dimensional density array representing the object using the corrected estimated densities of the portions of the object. The at least one beam of radiation may be a plurality of beams of radiation oriented in different perspectives. The measured attenuated portion of each of at least one beam of radiation may include a transmitted portion of a first beam of the at least one beam and a scattered portion of a second beam of the at least one beam. Determining a predicted attenuated portion of the at least one beam using the density estimate may include determining a predicted transmitted portion of the first beam using a density estimate and determining a predicted scattered portion of the second beam using a density estimate. The signal difference may include a transmitted signal difference and a scattered signal difference. Comparing the predicted attenuated portion to the measured attenuated portion to determine a signal difference may include comparing the predicted transmitted portion to the measured transmitted portion to determine a transmitted signal difference and comparing the predicted scattered portion to the measured scattered portion to determine a scattered signal difference.

Adjusting the density estimate of the portion of the object by scaling the density estimate using signal differences of rays that intersect the portion of the object may include adjusting the density estimate of the portion of the object by scaling the density estimate using transmitted signal differences of rays that intersect the portion of the object. Adjusting the density estimate of the portion of the object by scaling the density estimate using signal differences of rays that intersect the portion of the object may include adjusting the density estimate of the portion of the object by scaling the density estimate using scattered signal differences of rays that intersect the portion of the object. Adjusting the density estimate of the portion of the object by scaling the density estimate using signal differences of rays that intersect the portion of the object may include making an adjustment of the density estimate of the portion of the object by scaling the density estimate using scattered signal differences of rays that intersect the portion of the object and making another adjustment of the density estimate of the portion of the object by scaling the density estimate using transmitted signal differences of rays that intersect the portion of the object.

The first beam and the second beam may be one beam. The first beam and the second beam may be oriented in different perspectives. The measured attenuated portion may be a measured transmitted portion and the predicted attenuated portion may be a predicted transmitted portion. The measured attenuated portion may be a measured scattered portion and the predicted attenuated portion may be a predicted scattered portion. The at least one beam of radiation from the radiation source may have a plurality of energies. The method may include approximating the boundary of the object using a three-dimensional surface scan. The method may include initially estimating the density of the portions of the object within the boundary.

An embodiment of a method for three-dimensional image reconstruction includes obtaining a measured attenuated portion of a beam of radiation, the beam having been attenuated by interaction with an object, determining a predicted attenuated portion of the beam of radiation use a density estimate, and iteratively adjusting the density estimate the object by comparing the predicted attenuated portion and the measured attenuated portion. The predicted attenuated portion is re-determined once the density estimate is adjusted. The method may include generating a three-dimensional density array representing the object using the adjusted density estimate. The density estimate may be iteratively updated until a difference between consecutive density estimates is below a selected threshold or a predetermined number of iterations have been completed. The attenuated portion of the beam may include a scattered portion and a transmitted portion.

DETAILED DESCRIPTION

Figure 1:
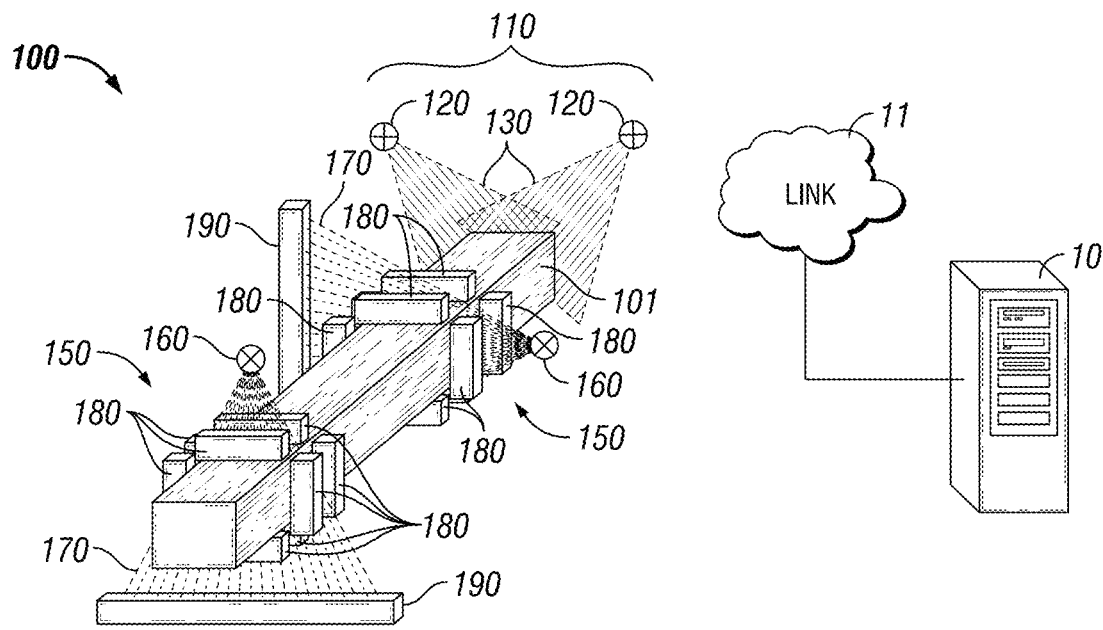
FIG. 1 shows an embodiment of an inspection system for inspecting objects translating through the inspection system.

Although the disclosure is described with respect to inspection of railway components, such as crossties, it is foreseeable that the disclosure is applicable to other industries as well. Applications of this method and system include nondestructive testing, security scanning, material identification, and medical applications.

In 2015, approximately 13 billion tons of freight was transported in the US, roughly 40 tons per person. 40% of all freight on a ton-mile basis will be transported by railroads. Class I railroads have approximately 140,000 miles (224,000 km) of railroad track across the country. Approximately 3,200 crossties per mile secure the rails at the proper gauge, transmit loads to the ballast, and prevent lateral and longitudinal shifting. Wood crossties can fail in many ways including rotting, breaking, cracking, and splitting. Accordingly, it is desirous to develop a system and method to inspect crossties in order to maintain and ensure safe railroad operations.

The railroad industry also has a need for a high-speed high-resolution 3D inspection method to inspect approximately 20 million newly fabricated railroad crossties per year. Currently new ties are not radiographically inspected to identify internal flaws and, for example, verify that rot prevention treatments have adequately penetrated into the crosstie. Further, known spiral scan CT systems are incapable of performing at the speed of a typical crosstie production line, which operates at 100-400 cm/s.

A method of inspecting and reconstructively modeling objects includes generating backscatter images and transmission images. The reconstruction method also incorporates transmission and scattering physics across a range of energies. The method combines transmission and scatter radiography in a plurality of orientations. Transmission radiography methods are based on the line attenuation between two points. Scatter X-ray imaging is dependent on the combination of the illumination beam attenuation, total scatter signal from the intersection of the illumination beam and detector field of view, and the attenuation of scattered X-rays.

Although the disclosure is described with reference to X-rays, it is foreseeable that this disclosure may benefit from the use of other energy sources as well, such as gamma rays from radioisotopes. A radioisotope may result in more accurate reconstructions, better penetration, and simpler rejection of higher order scatter noise reduction through the rejection of secondary scatters. Further, gamma rays may stimulate fluorescents. However, for safety reasons, some industrial environments may choose to use an X-ray source which could be turned off. Further, safety and regulatory compliance concerns may limit the applicability and placement of radioactive materials.

The inspection method may be performed without moving or rotating the radiation sources or detectors. The object may be translated through a stationary scanning system and an inspection may be performed at faster scanning speeds than with known methods. Internal inspection systems and surface inspection systems may be used to inspect the object.

The internal inspection system includes at least one radiation source, such as a gamma ray source, X-ray tube, or X-ray accelerator. In some embodiments, gamma ray sources and x-ray sources are used within the same system. X-ray sources may operate at different peak energies and include different filtering. In some embodiments, radiation sources having different energies may be used in the same perspective. One or more radioactive isotopes may be combined in the gamma source. The radiation sources may not be equidistant from a central point.

The radiation source may be collimated into directed beams, such as a fan beam or conical beam that permits the internal inspection of an object. The radiation source is positioned to irradiate a portion of an object with the collimated beam. Transmission detectors are positioned to receive a transmitted portion of the beam.

The transmission detectors are positioned within the illumination field of the radiation source on the opposite side of the object. The transmission detectors may be a linear detector array (1D), flat panel array (2D), or 3D array of stacked detector elements. Transmission detectors may be linear, planar, curved, or angled about the object. The transmission detectors may include filters or filtering materials to filter lower energy photons. The transmission detectors may be configured to integrate all photons of all energies or to provide energy information for each photon detected. The transmission detectors may not be equidistant from a corresponding radiation source.

After penetrating into the object, a portion of the beam of radiation is scattered, such that it rebounds or bounces from within the object. Scatter detectors are positioned to receive these scattered beams. The scatter detectors are positioned outside the illumination field of the radiation source to receive backscatter, side scatter, and forward scatter. The scatter detectors may include filters or filtering materials to filter lower energy photons. The scatter detectors may be configured to integrate all photons of all energies or to provide energy information for each photon detected. Collimation fins or grids may be positioned relative to the scatter detectors to prevent the detection of scattered rays from beyond a selected field of view within the object. The internal inspection system may include the Aurora Xi system from Georgetown Rail Equipment Company of Georgetown, Tex., and/or a system as disclosed in U.S. Pat. No. 9,031,188, issued on May 12, 2015, and entitled "Internal Imaging System," the disclosure of which is incorporated by reference in its entirety. The fields of view and collimation of the scatter detector arrays may be selected to provide unique scatter perspectives. The system may include filters for the scatter detectors or use detectors which are energy sensitive to improve the importance of first scatter photons to higher order scatter and noise.

The surface scanning subsystem includes scanning sources, such as laser or optical scanners, configured to provide a visual scan of the surface profile of an object. The surface inspection system may include the Aurora system from Georgetown Rail Equipment Company of Georgetown, Tex., and/or a system as disclosed in U.S. Pat. No. 9,441,956, issued on Sep. 13, 2016, and entitled "System and Method for Inspecting Railroad Ties," the disclosure of which is incorporated by reference in its entirety.

A computer processing unit (CPU) is in communication with the internal inspection system and the surface inspection system via a communications link. The communications link may be any combination of cable, wireless, or remote connection that provides electrical communication between the CPU and the internal inspection system and the surface inspection system. The CPU may include one or more memories for storing instructions and data. The instructions may when executed by the CPU initiate operations of the internal inspection system and/or the surface inspection system. Data is generated from each of the internal inspection system and the surface inspection system, which may be received by the CPU. The data may be used to analyze characteristics and densities of the object. The CPU may be programmed with various algorithms used to analyze the data and identify potential flaws and/or defects in the internal structure of the object. The CPU algorithms may be configured to implement the methods described herein. In some embodiments, the analyzing and processing may be performed on the same CPU or another CPU. For example, the internal inspection system may be mounted to a rail traversing vehicle or along an inspection path to collect data. The data may be stored and later processed off-site. In some embodiments, the data may be processed on-site. The CPU or another CPU may be used to create a three-dimensional reconstruction of the object using the data from the surface and internal inspection systems. Data received from the surface inspection system may be used to determine boundaries of an object to be inspected and to disregard objects outside of the region of interest, such as air. During reconstruction, voxels within the surface profile of the object are given an initial characteristic estimate, such as a uniform density.

Data received from the internal inspection system may be used to determine internal characteristics of the object. Radiation scatter from within an object may be used to determine the composition and other characteristics of the object. For example, different thickness of steel and copper may appear identical based only on transmission radiation and therefore, be indistinguishable. However, steel and copper will not scatter radiation in the same way. Measured values of transmission and/or scatter radiography may be compared with a predicted value to determine the accuracy of the internal characteristics of the object. The predicted and measured values are then compared to determine refined estimates of the internal characteristics. This process is repeated until the estimate of the internal characteristics is within a selected confidence interval. By combining transmission and scatter radiography, reconstructions can be more accurate than if only one radiography mode is used. Further, by using data from a surface scanning system, initial estimates may be more accurate and decrease the number of iterations needed to accurately estimate the internal characteristics.

FIG. 1 shows an inspection system 100 for inspecting objects by moving the object through the inspection system 100. By way of example, the object may be a crosstie 101, train, package, or container. The inspection system 100 includes a surface scanning subsystem 110 and a plurality of internal scanning subsystems 150. The surface scanning subsystem 110 includes scanning sources 120 configured to project beams 130 across a crosstie 101 within the inspection system 100. The scanning sources 120 may be laser or optical scanners. The scanning sources 120 may be orthogonally oriented with respect to each other. A surface profile of the crosstie 101 is acquired by the scanning sources 120 and used to determine which voxels in the reconstruction region are treated as existing outside the boundary of the crosstie 101, as is described in more detail below.

Figure 6A:
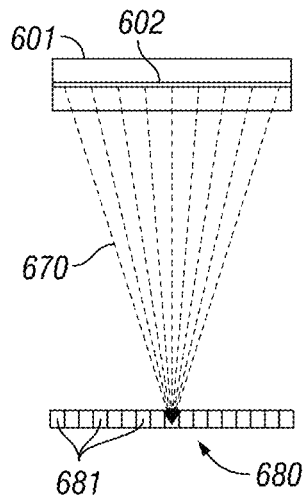
FIGS. 6A-C show an embodiment of a scatter detector with collimating fins.
Figure 6B:
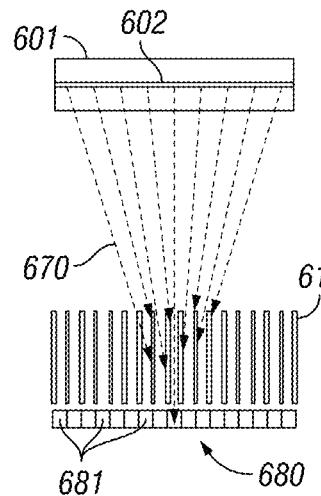
Figure 6C:
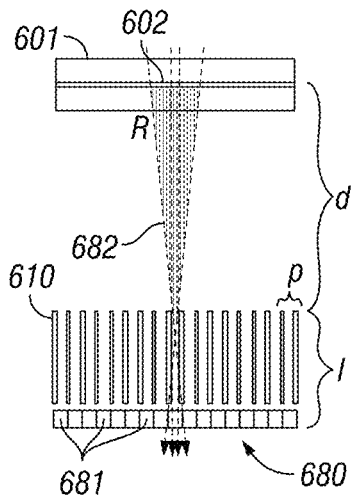

The internal scanning subsystems 150 each include a radiation source 160, a plurality of scatter detectors 180, and a transmission detector 190. The transmission detector 190 may be a linear detector array (1D), flat panel array (2D), or 3D array of stacked detector elements. The transmission detector 190 may be linear, planar, curved, or angled about the object. The radiation source 160 may be a gamma ray source, X-ray tube, or X-ray accelerator. Each radiation source 160 is configured to project a beam 170 across crosstie 101. The beam 170 may be a collimated fan beam or cone beam. The cone beam may be a small angle cone beam, such as a pencil beam. The transmission detector 190 is positioned opposite from the radiation source 160 to receive the beam 170 and sample the transmission perspective of the fan beam 170. Scatter detectors 180 are statically positioned around the path of travel of the crosstie 101 and sample the scatter perspectives of the fan beam 170 once it has been scattered by the crosstie 101. The scatter detectors 180 use collimated or limited fields of view to selectively detect back scatter, forward scatter, and side scatter of the beam 170 as the crosstie 101 is translated through the inspection system 100. For example, scatter detectors 180 may be positioned on a side of the crosstie 101 closest to the radiation source 160 to detect backscatter. Additional scatter detectors 180 may be statically positioned on a plurality of sides of the crosstie 101. The scatter detectors 180 may be orientated substantially orthogonally to other scatter detectors 180. An array of scatter detectors 180 may be positioned up the inspection line from the beam 170 and an array of detectors 180 may be positioned down the inspection line from the beam 170. The scatter detectors 180 may be linear detector arrays 680 with segmented collimation as shown in FIGS. 6A-C. The scatter detectors 180 may be two-dimensional detector arrays with two-dimensional collimation grids.

Additional internal scanning subsystems 150 may be statically positioned about the crosstie 101. For example, two or more offset internal scanning subsystems 150 may be oriented at 90 degrees with respect to each other, as shown in FIG. 1. In some embodiments, four offset internal scanning subsystems 150 are uniformly oriented around the perimeter of a crosstie 101.

The inspection system 100 includes a CPU 10 in communication with the surface scanning subsystem 110 and the internal scanning subsystems 150 via a link 11. The link 11 may be any combination of cable, wireless, or remote connection that provides electrical communication between the CPU 10 and the inspection system 100. The CPU 10 may include one or more memories for storing instructions and data. The instructions may when executed by the CPU 10 initiate operations of the surface scanning subsystem 110 and/or the internal scanning subsystems 150. Data is generated from each of the surface scanning subsystem 110 and/or the internal scanning subsystems 150, which may be received by the CPU 10. The data may be used to analyze characteristics and densities of the object being inspected. The CPU 10 may be programmed with various algorithms used to analyze the data and identify potential flaws and/or defects in the internal structure of the object. The algorithms may be configured to implement the methods described herein. In some embodiments, the analyzing and processing may be performed on the same CPU 10 or another CPU. For example, the data may be stored and later processed off-site. In some embodiments, the data may be processed on-site. The CPU 10 or another CPU may be used to create a three-dimensional reconstruction of the object using the data from the surface scanning subsystem 110 and/or the internal scanning subsystems 150.

Figure 2:
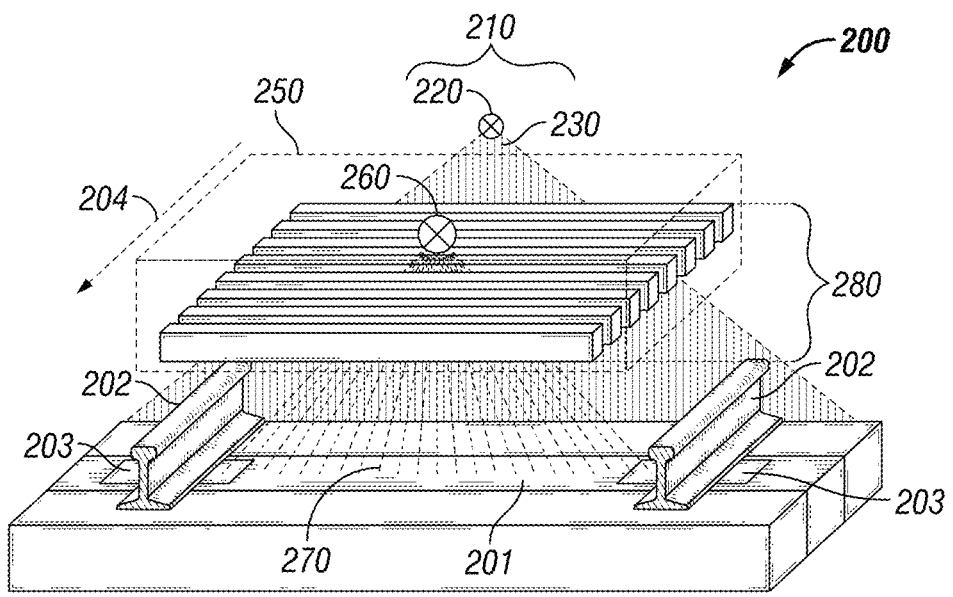
FIG. 2 shows an embodiment of an inspection system for inspecting installed railroad components between the rails.
Figure 4:
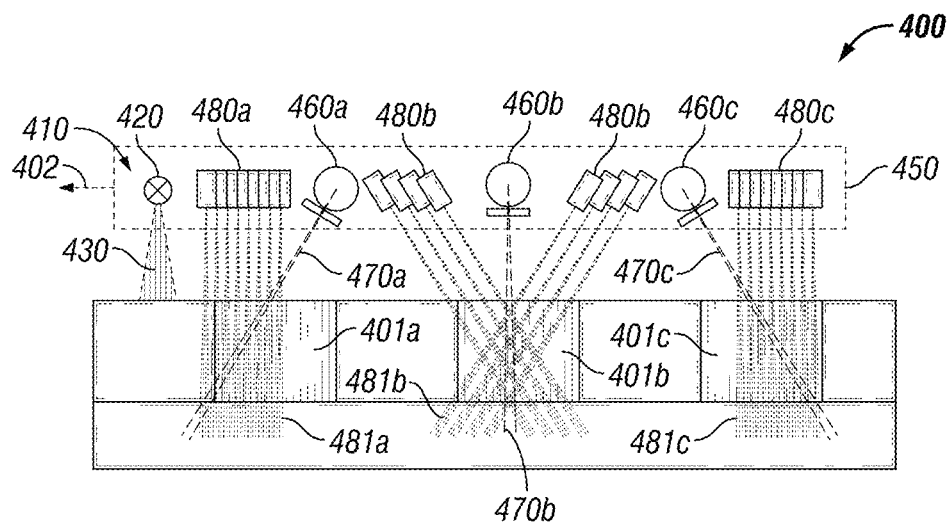
FIG. 4 shows an embodiment of an inspection system for inspecting installed railroad components.

FIG. 2 shows an inspection system 200 for inspecting installed railroad components between the rails 202. The railroad components may include various railroad components, such as, but not limited to crossties 201, tie plates 203, rails 202, spikes, fasteners, welds, and joint bars. The inspection system 200 may be mounted to a vehicle, such as a hi-rail vehicle or train car, configured to travel along the rails 202. The system 200 includes a surface scanning subsystem 210 and at least one internal scanning subsystem 250. As shown in FIG. 4, the inspection system 200 traverses the rails 202 in a first direction 204. It is appreciated, however, that inspection may occur in an opposite direction. The surface scanning subsystem 210 includes a scanning source 220 configured to project a beam 230 across the railroad components. The scanning source 220 may be a laser or optical scanner. A surface profile of the railroad component is acquired by the scanning source 220 and used to determine which voxels in the reconstruction region are treated as existing outside the boundary of the railroad component, such as air, as is described in more detail below.

The internal scanning subsystems 250 each include a radiation source 260 and a plurality of scatter detectors 280. The radiation source 260 may be a gamma ray source, X-ray tube, or X-ray accelerator. Each radiation source 260 is configured to project a beam 270 into the railroad component. The beam 270 may be a collimated fan beam. Scatter detectors 280 are positioned above the railroad track and sample the scatter perspectives of the beam 270 once it has been scattered by the railroad component. The scatter detectors 280 selectively detect scattered radiation from different volumetric regions of the railroad component. An array of scatter detectors 280 may be positioned on a first side of the beam 270 and an array of detectors 280 may be positioned on the other side of the beam 270. The scatter detectors 280 on the first side of the beam 270 may detect radiation scattered along the direction of travel 204. The scatter detectors 280 on the other side of the beam 270 may detect radiation scattered against the direction of travel 204. The scatter detectors 280 may be linear detector arrays 680 with segmented collimation as shown in FIGS. 6A-C. The scatter detectors 280 may be two-dimensional detector arrays with two-dimensional collimation grids.

Figure 3:
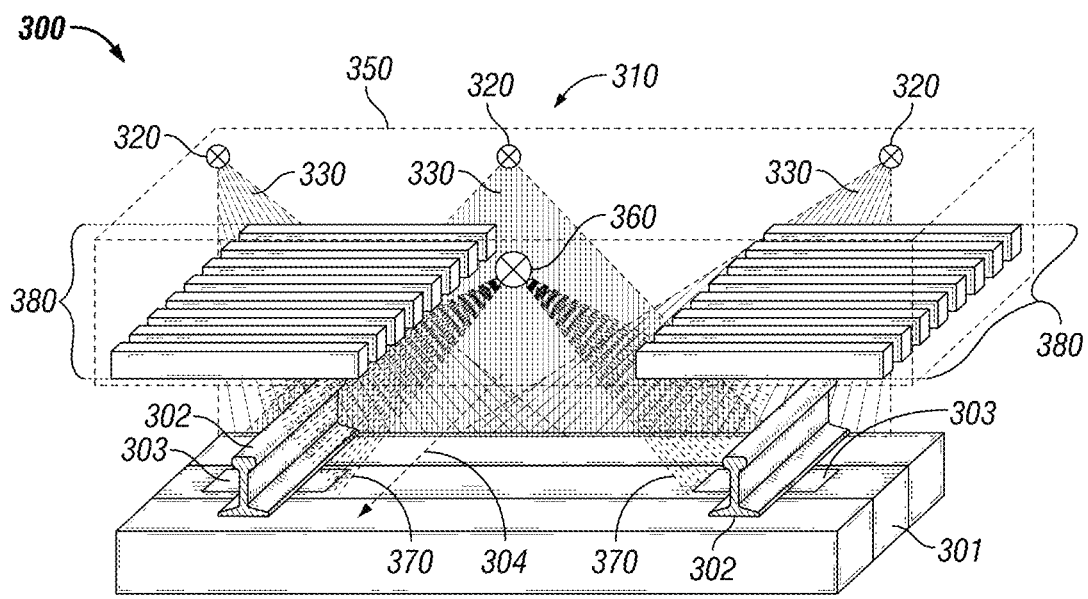
FIG. 3 shows an embodiment of an inspection system for inspecting installed railroad components across a railroad track.

FIG. 3 shows an inspection system 300 for inspecting installed railroad components across a railroad track. The railroad components may include crossties 301, tie plates 303, rails 302, spikes, fasteners, welds, and joint bars and various other components as would be appreciated by one of ordinary skill in the art having the benefit of this disclosure. The inspection system 300 may mounted to a vehicle, such as a hi-rail vehicle or train car, configured to travel along the rails 302. The inspection system 300 includes a surface scanning subsystem 310 and an internal scanning subsystem 350. The inspection system 300 traverses the rails 302 in a first direction 304. It is appreciated, however, that inspection may occur in an opposite direction. The surface scanning subsystem 310 includes a plurality of scanning sources 320 configured to project a beam 330 across the railroad components. One scanning source 320 may be oriented to scan the region between the rails of a railroad track. Other scanning sources 320 may be configured to scan another area of interest, such a rail 302 and tie plate 303. The scanning sources 320 may be a laser or optical scanner. A plurality of scanning sources 320 may be orthogonally oriented with respect to each other, as shown by the outer scanning sources 320 in FIG. 3. A surface profile of the railroad track is acquired by the scanning sources 320 and used to determine which voxels in the reconstruction region are treated as existing outside the boundary of the railroad track, such as air, as is described in more detail below.

The internal scanning subsystem 350 includes a radiation source 360 and a plurality of scatter detectors 380. The radiation source 360 may be a gamma ray source, X-ray tube, or X-ray accelerator. The radiation source 360 is configured to project a plurality of beams 370 into the railroad component. As shown in FIG. 3, the beams 370 may be projected across the inner portions of the rails 302 and directed to the portion of crossties 301 positioned beneath the rails 302. The beams 370 may be collimated fan beams. Scatter detectors 380 are positioned above the railroad track to receive scattered radiation from beams 370. An array of scatter detectors 380 may be positioned on a first side of the beam 370 and an array of detectors 380 may be positioned on the other side of the beam 370. The detectors 380 selectively detect backscattered radiation from different volumetric regions of the railroad component. Each beam 370 may have a corresponding array of scatter detectors 380 that samples the scatter perspectives of the corresponding beam 370 once it has been scattered by the railroad component. The scatter detectors 380 on the first side of the beams 370 may detect radiation scattered along the direction of travel 304. The scatter detectors 380 on the other side of the beams 370 may detect radiation scattered against the direction of travel 304. The scatter detectors 380 may be linear detector arrays 680 with segmented collimation as shown in FIGS. 6A-C. The scatter detectors 380 may be two-dimensional detector arrays with two-dimensional collimation grids.

FIG. 4 shows an inspection system 400 for inspecting installed railroad components. The inspection system 400 may be mounted to a vehicle, such as a hi-rail vehicle or train car, configured to travel along the rails. The inspection system 400 traverses the rails in a first direction 402. It is appreciated, however, that inspection may occur in an opposite direction. The system 400 includes a surface scanning subsystem 410 and an internal scanning subsystem 450. The surface scanning subsystem 410 acquires a surface profile of the railroad track, which is used to determine which voxels in the reconstruction region are treated as existing outside the boundary of the railroad track, such as air, as is described in more detail below. The surface scanning subsystem 410 may include at least one scanning source 420 configured to project a beam 430 across a portion of the railroad track.

Internal scanning subsystem 450 include radiation sources 460a, 460b, and 460c and a plurality of scatter detectors 480a, 480b, and 480c. The radiation sources 460a, 460b, and 460c may be a gamma ray source, X-ray tube, an X-ray accelerator, or a combination thereof. Each radiation source 460a, 460b, and 460c is configured to project a beam 470a, 470b, and 470c into a portion of the railroad track. A first radiation source 460a may be oriented towards an oncoming crosstie 401a. An array 480a of scatter detectors may be positioned in front of the radiation source 460a to detect backscatter of beam 470a. Each backscatter detector in the array 480a is configured to receive backscatter from a different volume within the railroad component along a resolution area 481a. A second radiation source 460b may be oriented towards a portion of the track, such as a crosstie 401b, directly below the second radiation source 460b. Corresponding arrays 480b of scatter detectors may be positioned in front and behind the radiation source 460b to detect backscatter of beam 470b. Each backscatter detector in the array 480b is configured to receive backscatter from a different volume within the railroad component along a resolution area 481b. A third radiation source 460c may be oriented toward an outgoing crosstie 401c. An array 480c of scatter detectors may be positioned behind the radiation source 460c to detect backscatter of beam 470c. Each backscatter detector in the array 480c is configured to receive backscatter from a different volume within the railroad component along a resolution area 481c. A railroad component being inspected may be sequentially inspected in different illumination perspectives as internal scanning subsystem 450 travels along the rails, such as by the beam 430 of surface scanning subsystem 410, then beam 470a of radiation source 460a, then beam 470b of radiation source 460b, and by beam 470c of radiation source 460c. The scatter detectors 480a, 480b, and 480c may be linear detector arrays 680 with segmented collimation as shown in FIGS. 6A-C. The scatter detectors 480a, 480b, and 480c may be two-dimensional detector arrays with two-dimensional collimation grids. In some embodiments, radiation sources 460a, 460b, and 460c may be the same radiation source configured to project a plurality of beams 470a, 470b, 470c.

Figure 5:
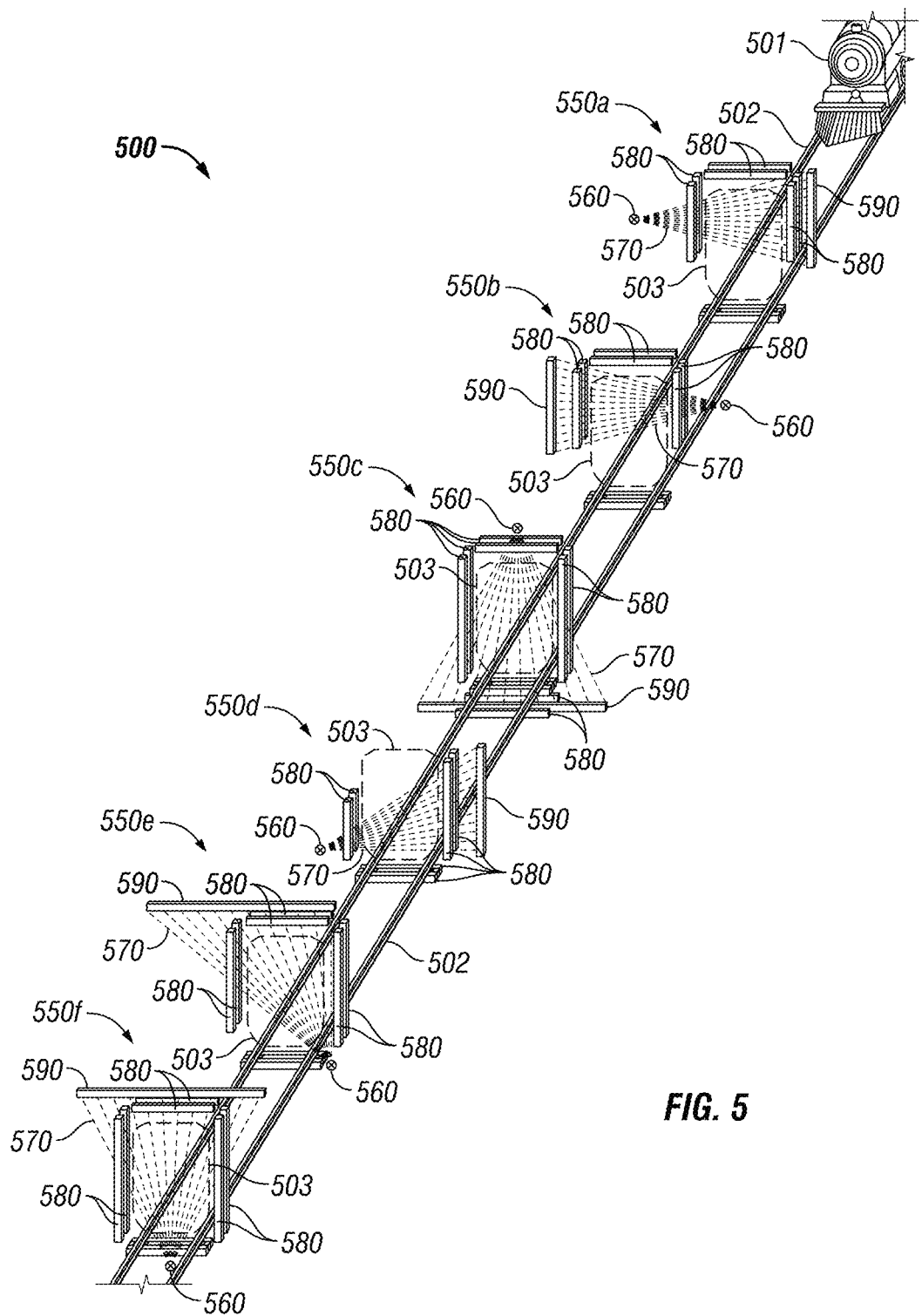
FIG. 5 shows an embodiment of an inspection system with a plurality of illumination perspectives for inspecting objects by moving the object through the inspection system along a travel path.

FIG. 5 shows an inspection system 500 for inspecting objects by moving the object through the inspection system 500 along a travel path 502. By way of example, the object may be a crosstie, container, vehicle, or a train 501. The system 500 may be sized to Association of American Railroads (AAR) clearance standards, such as AAR Plate C, to receive a car of the train 501 to be inspected, as would be appreciated by one of ordinary skill in the art having the benefit of this disclosure. The system 500 includes a plurality of internal scanning subsystems 550a-f orientated at a plurality of illumination perspectives. Although inspection system 500 is shown to include six illumination perspectives, other combinations of these perspectives and other perspectives are possible as would be appreciated by one of ordinary skill in the art having the benefit of this disclosure. Each illumination perspective may be selected to provide unique transmission and scatter perspectives. The illumination perspectives may be selected such that each volumetric region within the object is illuminated by two or more substantially orthogonal illumination perspectives as it travels through the inspection system 500.

Addition illumination perspectives may increase the resolution of the reconstruction. For example, in some perspectives, scatter detectors 580 may only be positioned to receive scattered radiation from a portion of a dimension of the train 501 near scatter detectors 580. In some perspectives, radiation sources 560 are directed at only a portion of train 501 within travel path 502. Radiation sources 560 may be oriented orthogonally, toward an oncoming, or toward an outgoing portion of train 501 within travel path 502. Likewise, the orientation of radiation sources 560 may also provide different transmission perspectives to be received by linear detectors 590. The internal scanning subsystems 550a-f may be offset from each other and not simultaneously illuminate the same volume of train 501. A profile 503 of train 501 is shown at various points along travel path 502 as it intersects an illumination perspective of the internal scanning subsystems 550A-f.

The internal scanning subsystems 550a-f each include a radiation source 560, a plurality of scatter detectors 580, and a transmission detector 590. The transmission detector 590 may be a linear detector array (1D), flat panel array (2D), or 3D array of stacked detector elements. The transmission detector 590 may be linear, planar, curved, or angled about the train 501. The transmission detector 590 may be positioned above the train 501, such as shown in internal scanning subsystems 550e and 550f. The transmission detector 590 may be positioned below the train 501, such as shown in internal scanning subsystem 550c. The radiation source 560 may be a gamma ray source, X-ray tube, or X-ray accelerator. Each radiation source 560 is configured to project a beam 570 into train 501. The beam 570 may be a collimated fan beam or cone beam. The cone beam may be a small angle cone beam, such as a pencil beam. Scatter detectors 580 are statically positioned around the travel path 502 of the train 501 and sample the scatter perspectives of the fan beam 570 once it has been scattered by train 101. Scatter detectors 580 are statically positioned on at least one side of train 501. Additional scatter detectors 580 may be statically positioned on a plurality of sides of train 501. The scatter detectors 580 may be orientated substantially orthogonally to other scatter detectors 580. An array of detectors 580 may be positioned up the inspection line from the beam 570 and an array of detectors 580 may be positioned down the inspection line from the beam 570. The detectors 580 selectively detect back scatter, forward scatter, and side scatter of the beam 570 as train 501 travels through inspection system 500 along travel path 502. In some embodiments, the scatter detectors 580 are non-symmetrical in size and placement relative to other illumination perspectives. The scatter detectors 580 may be linear detector arrays 680 with segmented collimation as shown in FIGS. 6A-C. The scatter detectors 580 may be two-dimensional detector arrays with two-dimensional collimation grids.

A radiation source 560 of an internal scanning subsystem 550a-f may be configured to simultaneously irradiate separate portions of the same object in different perspectives. For example, the radiation source 560 may project a plurality of beams oriented in different directions. The plurality of beams may be oriented orthogonally to the object, toward an oncoming portion of the object, toward an outgoing portion of the object, or combinations thereof. The radiation source 560 might be radiation sources 460a, 460b, and 460c, as discussed above with respect to FIG. 4. In some embodiments, the same illumination perspective may be repeated with different radiation sources, such as x-ray and gamma rays. The same internal scanning subsystem 550a-f may be reoriented with respect to the object or train 501 and a subsequent scan may be used to provide a new illumination perspective using the same internal scanning subsystem 550a-f. Alternatively, the orientation of the object may be changed and a subsequent scan may be used to provide a new illumination perspective using the same internal scanning subsystem 550a-f.

FIGS. 6A-C show an embodiment of a scatter detector 680. The scatter detector 680 is a linear detector array with segmented collimation for each detector element 681. The segmented collimation limits the field of view of each scatter detector element 681 to a specific volume within the object 601. As illustrated in FIG. 6A, a radiation source (not shown) is configured to irradiate an object 601 with a beam of penetrating radiation 602. For purposes of clarity in explaining scatter detector 680, the beam of penetrating radiation 602 is shown as already having penetrated within the object 601. The beam 602 rebounds or bounces from within the object 601 as backscatter rays 670. The backscatter rays 670 are returned from the object 601 and received by scatter detector 680.

The scatter detector 680 may include collimating fins 610, as illustrated in FIG. 6B. Collimated fins 610 restrict the backscatter rays 670 that are received by a particular segmented detector element 681. The scatter detector 680 may be a two-dimensional detector array with two-dimensional collimation grids, as may be appreciated by one of ordinary skill in the art having the benefit of this disclosure. The collimating grid may comprise substantially orthogonal collimating fins 610 that restrict the backscatter rays 670 that are received by a particular two-dimensional segmented detector element 681. The collimating grid may comprise other shapes, such as parallel-holes, honeycomb, and pinhole collimators. Each backscatter detector element 681 is configured to receive backscatter from a field of view 682, as illustrated in FIG. 6C. The field of view 682 of the object 601 for a particular element 681 is dependent upon the distance d of the detector element 681 from the object 601, the length 1 of the collimating fins 610, and the distance p between the collimating fins 610. Accordingly, the approximate resolution R of the field of view 682 may be represented as $$R = 2\left(d + \frac{l}{2}\right)\left(\frac{p}{l}\right) = \frac{2dp}{l} + p.$$

Figure 7:
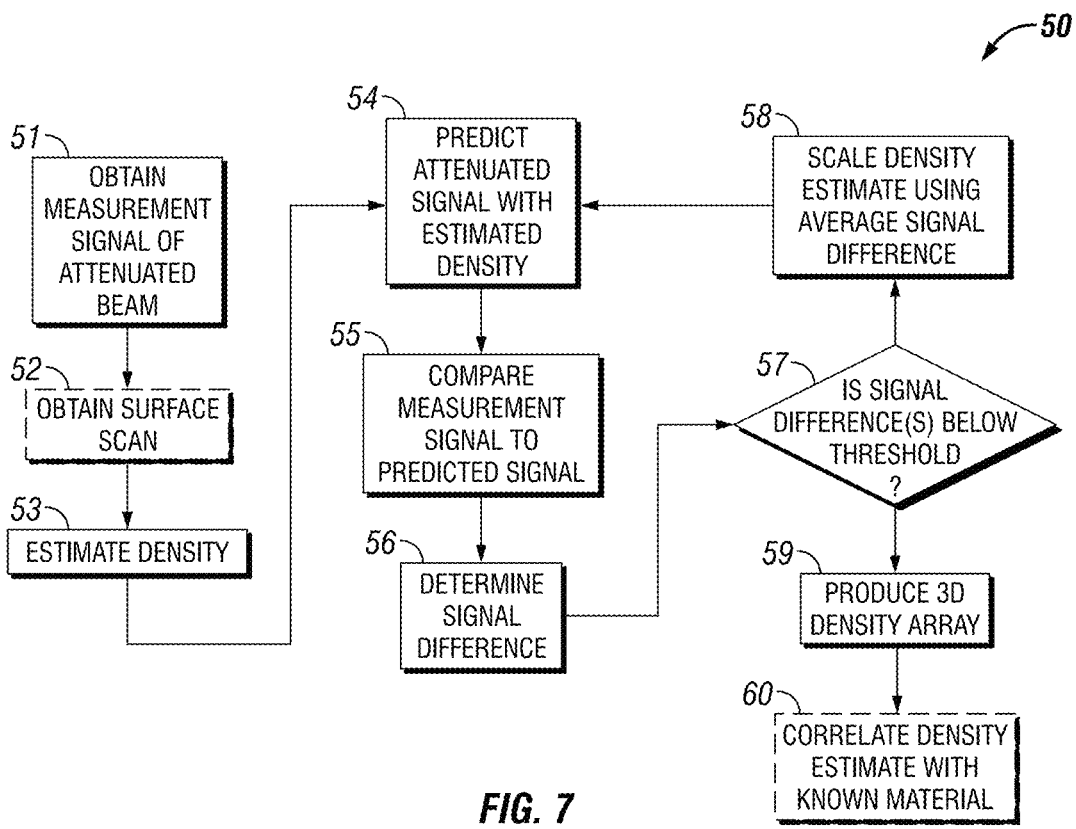
FIG. 7 shows a flow chart of one embodiment of a method for three-dimensional image reconstruction.

FIG. 7 shows a flow chart of one embodiment of a method for three-dimensional image reconstruction 50. The method 50 includes an Action 51 of measuring or otherwise obtaining an actual signal of an attenuated beam of radiation between a focal spot of a radiation source and a detector location that has been attenuated by interaction with an object. The detector is positioned to receive radiation that has been attenuated by interaction with the object. The method 50 may include an optional Action 52 of using a surface profile scan to obtain a surface scan and determine a boundary of the object. Each voxel within an object is given a density estimate in Action 53. The density estimate may be a uniform density. Voxels surrounding the object, such as air or other materials desired to be discarded, may be ignored or permanently treated as air in the three-dimensional reconstruction. Voxels within the boundary of the object may be initially estimated to be a uniform density. The method 50 includes an Action 54 of predicting an attenuated signal of radiation between the focal spot of a radiation source and the detector location using the initial normalized X-ray beam intensity spectra of and a radiation constant. The radiation constant may comprise constant terms, such as energy conversions between electron volt energies and detector signal levels. The radiation constant and initial normalized X-ray beam intensity spectra of may be determined using calibration of the radiation source. The initial normalized X-ray beam intensity spectra is dependent upon the radiation source. The extent of absorption of the X-rays within the object material is dependent upon the photon energy, the thickness of the material, and the composition of the material.

The method 50 iteratively converges the density of each voxel in the object region. The predicted attenuated signal is compared to the actual attenuated signal in Action 55. An attenuated signal difference of the predicted attenuated signal and the actual attenuated signal for each voxel along the ray between focal spot and detector location is determined in Action 56 as the ratio of the difference of the predicted attenuated signal and the actual attenuated signal to the actual attenuated signal.

In Decision 57, it is determined whether the attenuated signal difference is below a selected threshold or a predetermined number of adjustments have been completed, indicating a level of accuracy of the estimated density at the voxel. The difference between consecutive density estimates may also be shown by determining whether the attenuated signal difference is below a selected threshold, since the predicted attenuated signal is calculated using the density estimate. Using the attenuated signal difference, an initial density estimate for every voxel is scaled and estimated using the previous voxel density, a convergence constant, and the average of the attenuated signal differences of a subset of all rays which intersect the voxel in Action 58. The convergence constant may be estimated as the voxel density. An updated predicted attenuated signal is then calculated using the refined density estimate in place of the initial density estimate. A refined attenuated signal difference is then determined using the newly estimated predicted attenuated signal and the actual attenuated signal, which is then used to further refine the density estimate. The density estimate may be iteratively adjusted until the difference between consecutive density estimates is below the selected threshold in Decision 57.

Figure 8:
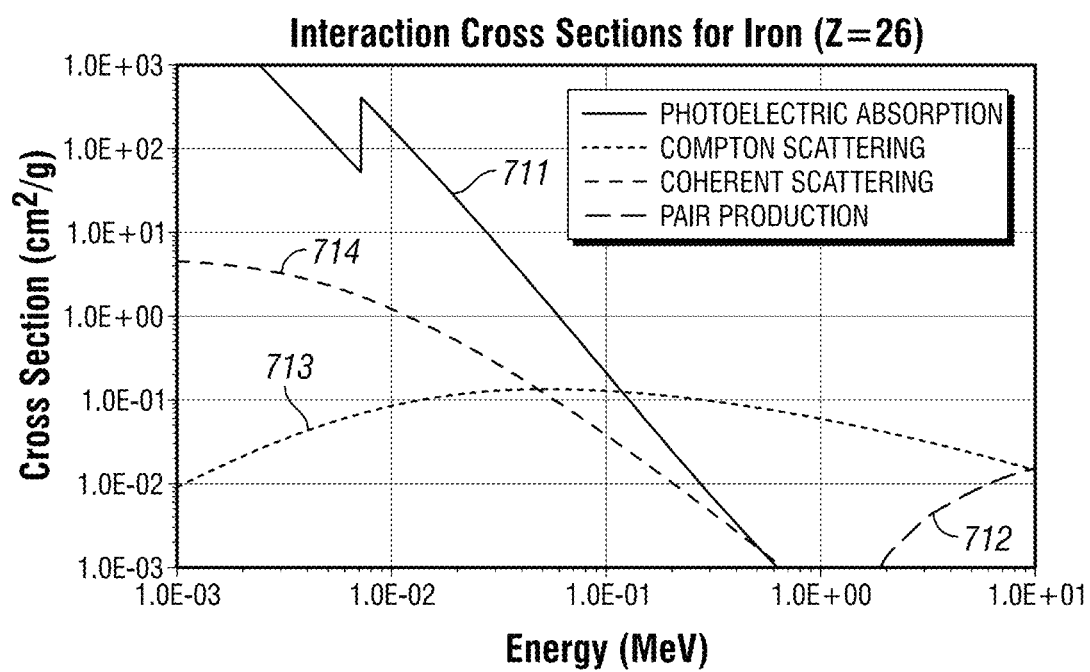
FIG. 8 shows example cross section data for iron.

Based upon the estimated density at each voxel, the method may include generating a three-dimensional density array representing the object in Action 59. The three-dimensional density array may be further processed to construct a three-dimensional reconstruction of the object, as would be appreciated by those of ordinary skill in the art having the benefit of this disclosure. The method 50 may include an optional Action 60 of correlating the estimated density with known materials, such as air, wood/paper, alcohol, water, tissue, bone, explosives, rock, concrete, aluminum, iron, lead, and uranium. For example, the cross sectional data for iron is shown in FIG. 8. The cross-sectional data includes a photoelectric absorption 711, a pair production 712, a Compton scattering 713, and a coherent scattering 714.

The method for three-dimensional image reconstruction may include only transmission radiography. The transmission signal $T_{B_i \to D_j}$ between a focal spot B of a radiation source and a detector location D is predicted by using the initial normalized X-ray beam intensity spectra of $\hat{I}_0(E)$ and a transmission constant $C_T$. The transmission constant $C_T$ may comprise constant terms, such as energy conversions between electron volt energies and detector signal levels. The transmission constant $C_T$ and initial normalized X-ray beam intensity spectra of $\hat{I}_0(E)$ may be determined using calibration of the radiation source. The object is positioned between focal spot B and detector location D. The initial normalized X-ray beam intensity spectra is dependent upon the radiation source. The extent of absorption of the X-rays within the object material is dependent upon the photon energy E, the thickness of the material, and the composition of the material. The predicted transmission signal $T_{B_i \to D_j}$ between any focal spot $B_i$ and detector location $D_j$ is predicted using the equation $$T_{B_i \to D_j} = C_T \int_{E=0}^{E_{max}} \frac{E \hat{I}_0(E)}{2\pi(|B_i - D_j|)} \exp\left(\int_{r=B_i}^{D_j} -\mu/\rho(E)\rho(r)dr\right) dE.$$

The method iteratively converges the density, $\rho(r)$, rather than the attenuation coefficient, $\mu/\rho(E)$, of each voxel in the object region. The attenuation coefficient $\mu/\mu(E)$ may be determined from NIST XCOM nuclear data and vary depending upon density along a path.

The actual transmission signal $M_{B_i \to D_j}$ is measured between the focal spot $B_i$ and the detector location $D_j$. A transmitted signal difference $\Delta_{T_n}$ of the predicted transmission signal $T_{B_i \to D_j}$ and the measured transmission signal $M_{B_i \to D_j}$ for each voxel along the ray between focal spot $B_i$ and detector location $D_j$ is determined using the equation $$\Delta_{T_n} = \frac{T_{B_i \to D_j} - M_{B_i \to D_j}}{M_{B_i \to D_j}}.$$

Using the transmitted signal difference $\Delta_{T_n}$, an initial density estimate for every voxel is refined and estimated using the previous voxel density, $\rho(V_r)^k$, a transmission convergence constant $\gamma_t$, and the average of the transmitted signal differences $\Delta_{T_n}$ of a subset of all rays A which intersect voxel $V_r$. The transmission convergence constant $\gamma_t$ may be estimated as the voxel density $\rho(V_r)^k$. Accordingly, the refined density estimate $\rho(V_r)^{k+1}$ is determined using the equation $$\rho(V_r)^{k+1} = \rho(V_r)^k \left(1 + \frac{\gamma_t}{A} \sum_{}^{A} \Delta_{T_a}\right).$$

An updated predicted transmission signal $T_{B_i \to D_j}$ is then calculated using the refined density estimate $\rho(V_r)^{k+1}$ in place of the initial density estimate $\rho(V_r)^k$. A refined transmitted signal difference $\Delta_{T_n}$ is then determined using the newly estimated predicted transmission signal $T_{B_i \to D_j}$, which is then used to further refine the density estimate. The density estimate may be iteratively adjusted until the difference between consecutive density estimates $\rho(V_r)^k$ and $\rho(V_r)^{k+1}$ is below a selected threshold, indicating a level of accuracy of the estimated density at the voxel. The difference between consecutive density estimates $\rho(V_r)^k$ and $\rho(V_r)^{k+1}$ may also be shown by determining whether the transmitted signal difference $\Delta_{T_n}$ is below a selected threshold, since the predicted transmission signal $T_{B_i \to D_j}$ is calculated using the density estimate.

Figure 9:
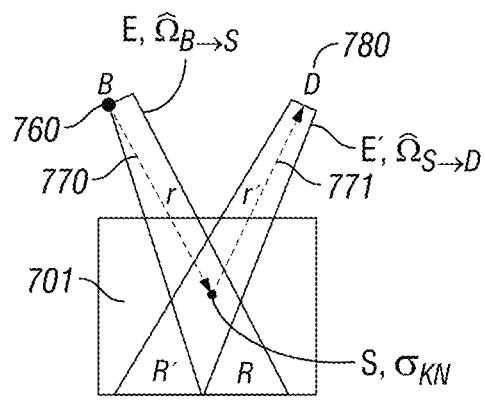
FIG. 9 partially illustrates scattering of radiation by an object.

The method for three-dimensional image reconstruction may include only scatter radiography. A scatter radiography system includes more degrees of freedom than a transmission-only radiography system. Radiation is directed into the object from a radiation source. Collimated detectors may be positioned around the object to detect scattered radiation from within the object. The partial scatter signal $S_{B_i \to D_j}$ is predicted from a focal spot location B of a radiation source to a single voxel V within the object to a detector element location D. As shown in FIG. 9, a radiation source 760 at focal spot B projects radiation 770 into an illuminated volume R of the object 701. The projected radiation has many initial energy levels E in a spectra $\hat{I}_0(E)$ and many slightly different vector directions $\hat{\Omega}$ within illumination field R. An individual ray 770 within a radiation illumination field R penetrates along ray r into the object 701 to scatter point S. The individual ray scatters from initial energy E to energy E' and changes vector direction from $\hat{\Omega}$ to $\hat{\Omega}'$. Scattered radiation 771 penetrates along ray r' within the detector field of view R' to a detector element 780 at location D. Although FIG. 9 is shown with respect to backscatter rays, a person of ordinary skill in the art having the benefit of this disclosure would appreciate that scattering in any direction may also occur according to the initial energy E and integrated Klein-Nishina cross section, discussed below. A partial scatter signal $S_{B_i \to V_r \to D_j}$ from a focal spot location $B_i$ to a single voxel $V_r$ at r is predicted using the equation $$S_{B_i \to V_r \to D_j} =$$

$$C_S \int_{E=0}^{E_{max}} \frac{E' \hat{I}_0(E)}{2\pi(|B_i - V_r|)} \exp\left(\int_{r=B_i}^{V_r} -\mu/\rho(E)\rho(r)dr\right) \frac{\rho(V_r)}{2\pi(|V_r - D_j|)} 2\pi \sin$$

$$\theta \sigma_{KN}\left(r, E \to E', \hat{\Omega} \to \hat{\Omega}'\right) \exp\left(\int_{r'=V_r}^{D_j} -\mu/\rho(E')\rho(r')dr'\right) dE.$$

The scatter energy level E' relative to the initial energy level E can be expressed as $$E' = \frac{E}{(1 + (E/m_0 c^2)(1 - \cos\theta))}.$$

$C_S$ is the scatter constant, $\hat{I}_0(E)$ is the normalized X-ray beam intensity spectra, $\sigma_{KN}$ is the Klein-Nishina scattering cross section into a solid angle from $\hat{\Omega} \rightarrow \hat{\Omega}'$, $\theta$ is the angle between vectors $\hat{\Omega} \rightarrow \hat{\Omega}'$, and $E \rightarrow E'$ is the Compton scatter change of energy. The scatter constant $C_S$ may comprise constant terms, such as energy conversions between electron volt energies and detector signal levels. The scatter constant $C_S$ and initial normalized X-ray beam intensity spectra of $\hat{I}_0(E)$ may be determined using calibration of the radiation source. The Klein-Nishina differential Compton scatter cross section per electron is represented as $$\frac{d\sigma_e}{d\Omega_\theta} = \frac{r_0^2}{2}\left(\frac{E'}{E_0}\right)^2\left(\frac{E_0}{E'} + \frac{E'}{E_0} - 1 + \cos^2\theta\right).$$

Figure 10:
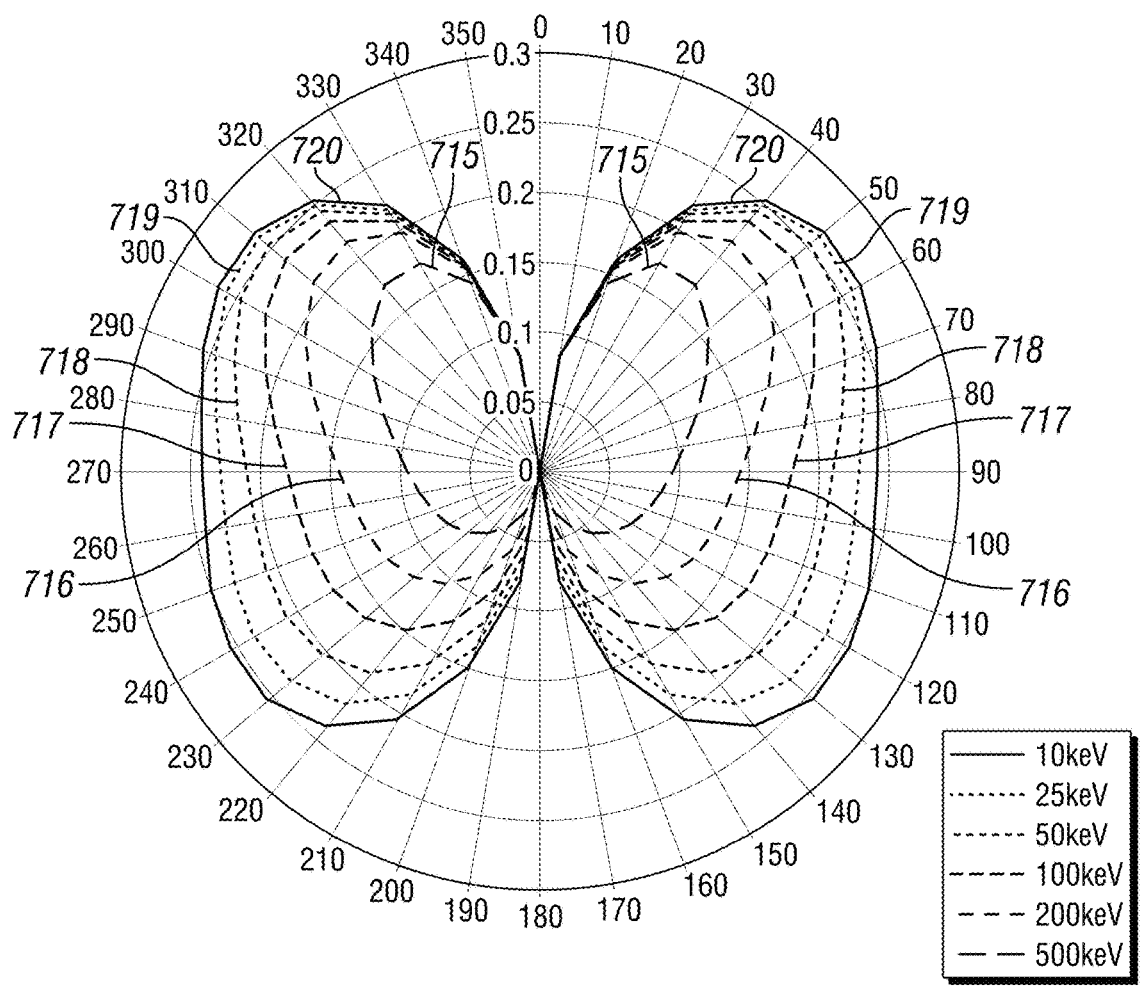
FIG. 10 shows a Klein-Nishina cross section at various energies per angle.

The integrated Klein-Nishina cross section, $\sigma_{KN}$, in cm²/atom is determined by integrating the differential Compton cross sections between $(0, \pi)$ and multiplying by the number of electrons per atom, Z. The Klein-Nishina cross section per angle is shown in FIG. 10 for a 500 keV energy 715, a 200 keV energy 716, a 100 keV energy 717, a 50 keV energy 718, a 25 keV energy 719, and a 10 keV energy 720. Thus, the total Klein-Nishina cross section, $\sigma_{KN}$, is represented as $$\sigma_{KN} = 2\pi \frac{N_A Z}{\rho} \int_{\theta=0}^{\pi} \frac{d\sigma_e}{d\Omega_\theta} \sin\theta d\theta.$$

A total scatter signal $S_{B_i \rightarrow D_j}$ detected by the segmented collimator detector between every focal spot $B_i$ and detector location $D_j$ is predicted. All of the partial scatter signals $S_{B_i \rightarrow V_r \rightarrow D_j}$ from all voxels $V_r$ within the intersection of the illumination volume R and the scatter detector element field of view, $V_R$, are combined and scaled by the fraction of photons which have only scattered once $F(O_1)$. It may be advantageous to scale the total signal detected by photons that have only scattered once because photons which have scattered more than once lose more energy and may originate from locations outside of the voxel of interest. The fraction of single scattered photons is computed by calibration, predicted with MCNP simulations, or minimized by using detectors which provide energy information for each detected photon. Accordingly the total signal detected is computed by equation $$S_{B_i \rightarrow D_j} = F(O_1)\Sigma_{V_r}^{V_R} S_{B_i \rightarrow V_r \rightarrow D_j}.$$

The method iteratively converges the density, $\rho(r)$, rather than the attenuation coefficient, $\mu/\rho(E)$, of each voxel in the object region.

The actual scatter signal $M_{B_i \rightarrow D_j}$ is measured between the focal spot $B_i$ and the detector location $D_j$. A scattered signal difference $\Delta_{S_m}$ of the predicted scatter signal $S_{B_i \rightarrow D}{}^j$ and the measured scatter signal $M_{B_i \rightarrow D_j}$ from all voxels, $V_R$, within the intersection of the illumination volume R and the scatter detector element field of view R' is computed using the equation $$\Delta_{S_m} = \frac{S_{B_i \rightarrow D_j} - M_{B_i \rightarrow D_j}}{S_{B_i \rightarrow D_j}}.$$

Using the scattered signal difference $\Delta_{S_m}$, an initial density estimate for every voxel is refined and estimated using the previous voxel density, $\rho(V_r)^k$, a scatter convergence constant $\gamma_s$ and the average of scattered signal differences $\Delta_{S_m}$ of the set B, where B is composed of all scatter detector elements with an intersecting field of view. The scatter convergence constant $\gamma_s$ may be estimated as the voxel density $\rho(V_r)^k$. Accordingly, the refined density estimate $\rho(V_r)^{k+1}$ is determined using the equation $$\rho(V_r)^{k+1} = \rho(V_r)^k\left(1 - \frac{\gamma_s}{B}\sum^B \Delta_{S_b}\right).$$

An updated predicted scatter signal $S_{B_i \rightarrow D_j}$ is then calculated using the refined density estimate $\rho(V_r)^{k+1}$ in place of the initial density estimate $\rho(V_r)^k$. A refined scatter signal difference $\Delta_{S_m}$ is then determined using the newly estimated predicted scatter signal $S_{B_i \rightarrow D_j}$, which is then used to further refine the density estimate. The density estimate may be iteratively adjusted until the difference between consecutive density estimates $\rho(V_r)^k$ and $\rho(V_r)^{k+1}$ is below a selected threshold, indicating a level of accuracy of the estimated density at the voxel. The difference between consecutive density estimates $\rho(V_r)^k$ and $\rho(V_r)^{k+1}$ may also be shown by determining whether the scatter signal difference $\Delta_{S_m}$ is below a selected threshold since the predicted scatter signal $S_{B_i \rightarrow D_j}$ is calculated using the density estimate.

The method for three-dimensional image reconstruction may include both scatter radiography and transmission radiography. Within each iteration, differences from both the transmission and scatter perspectives may be combined to successively estimate the next voxel densities to minimize the difference between predicted and measured signal intensity. The density estimate based on scatter radiography $$\rho(V_r)^{k+1} = \rho(V_r)^k\left(1 - \frac{\gamma_s}{B}\sum^B \Delta_{S_b}\right).$$

is combined with the density estimate based on transmission radiography $$\rho(V_r)^{k+1} = \rho(V_r)^k\left(1 + \frac{\gamma_t}{A}\sum^A \Delta_{T_a}\right)$$

to provide a density estimate based on both transmission radiography and scatter radiography $$\rho(V_r)^{k+1} = \rho(V_r)^k\left(1 + \frac{1}{A+B}\left(\sum^A \gamma_t \Delta_{T_a} - \sum^B \gamma_s \Delta_{S_b}\right)\right).$$

An updated predicted scatter signal $S_{B_i \rightarrow D_j}$ is then calculated using the refined density estimate $\rho(V_r)^{k+1}$ in place of the initial density estimate $\rho(V_r)^k$. A refined scattered signal difference $\Delta_{S_m}$ is then determined using the newly estimated predicted scatter signal which is then used to further refine the density estimate to $\rho(V_r)^{k+2}$. An updated predicted transmission signal $T_{B_i \rightarrow D}{}^j$ is then calculated using the refined density estimate $\rho(V_r)^{k+2}$. A refined transmitted signal difference $\Delta_{T_m}$ is then determined using the newly estimated predicted transmission signal which is then used to further refine the density estimate. The density estimate may be iteratively adjusted for all transmission and scatter detector signals until the difference between consecutive density estimates $\rho(V_r)^k$ and $\rho(V_r)^{k+1}$ is below a selected threshold, indicating a level of accuracy of the estimated density of the voxel. The difference between consecutive density estimates $\rho(V_r)^k$ and $\rho(V_r)^{k+1}$ may also be shown by determining whether the transmitted signal difference $\Delta_{T_q}$ and/or the scattered signal difference $\Delta_{S_m}$ is below a selected threshold since the predicted transmission signal $T_{B_i \to D_j}$ and predicted scatter signal $S_{B_i \to D_j}$ are calculated using the density estimate.

Although the combined density estimate assumes equal importance of scatter perspectives and transmission perspectives at any spatial location, optimal selection of the transmission and scatter convergence values $\gamma_s$ and $\gamma_t$ may lead to faster converging 3D reconstructions. Further, combinations of only transmission radiography, only scatter radiography, and/or the scatter & transmission radiographies may be applied in any order within a single density estimation iteration. For example, both the scatter signal and transmission signal predictions may be determined concurrently and used simultaneously to refine the density estimate. In other embodiments, the iterations may alternate between predicting a scatter signal, a transmission signal, or both.

Figure 11:
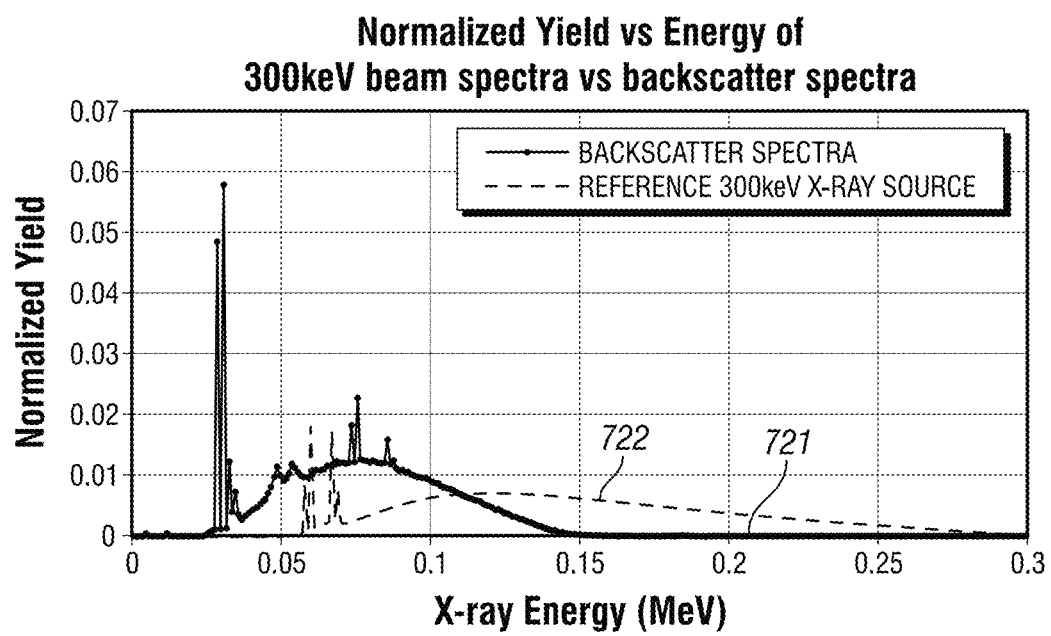
FIG. 11 shows a normalized filtered X-ray spectra with a peak energy of 300 keV and the associated backscatter spectra from wood.
Figure 12:
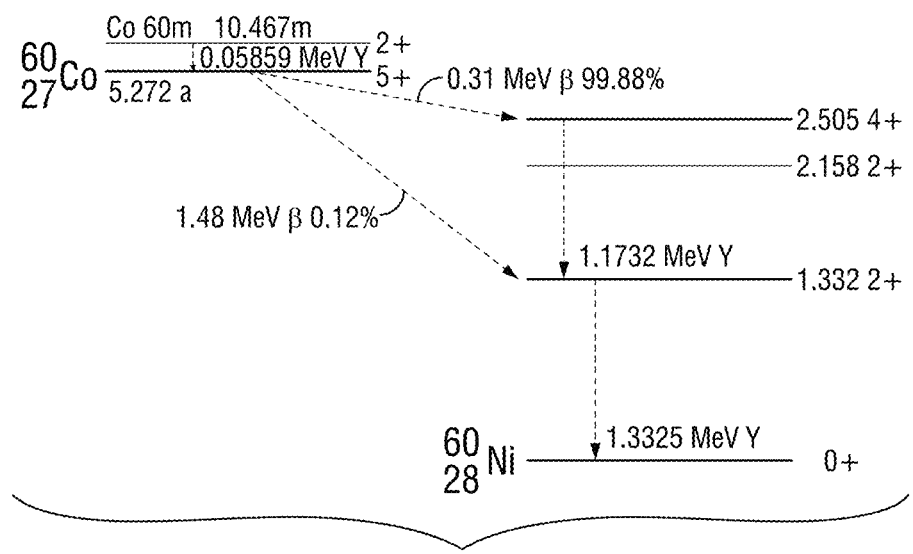
FIG. 12 shows the decay scheme and principal energies of a Co-60 radioisotope source.

It is beneficial to known the intensity and energy distribution $\hat{I}_0(E)$ of the radiation illumination source. FIG. 11 shows a normalized filtered X-ray spectra 722 with a peak energy of 300 keV and the associated backscatter spectra 721 from wood. FIG. 12 shows the decay scheme and principal energies of a Co-60 radioisotope source. Within the energy distribution of scattered and/or transmitted radiation, characteristic spikes can be used for material identification and quantity characterization.

EXAMPLE

Figure 13:
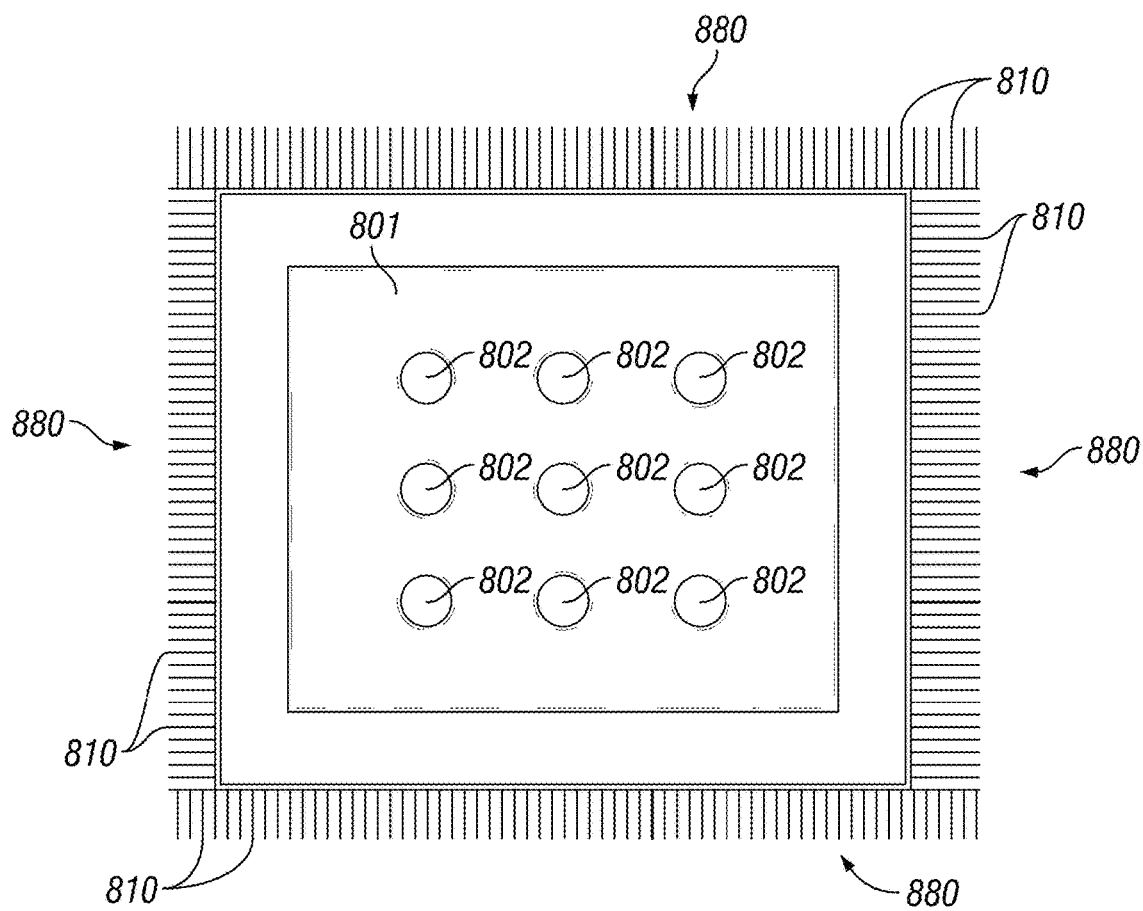
FIG. 13 shows a sample object with nine voids surrounded by an embodiment of segmented linear detectors with collimating fins.

MCNP models were generated to simulate the scatter and transmission perspectives of 2 cm diameter cylindrical void patterns within a 0.7 g/cc 22 cm×18 cm wood crosstie. FIG. 13 shows an example of nine voids 802 arranged in three rows and three columns within the crosstie 801 surrounded by collimating fins 810 of four segmented linear detector arrays 880.

A surface profile scan may be used to treat voxels surrounding the crosstie as air and to initialize voxels within boundary of the surface scan with a uniform estimate of crosstie density. The reconstruction method iteratively converges the density, not the attenuation coefficient, of each voxel in the object region by comparing the predicted signal and the measured signal. Ranges of densities are correlated with the cross sections of known materials such as air, wood, water, and iron. Within each iteration, differences from both the transmission and scatter perspectives are combined to successively estimate voxel densities to minimize the difference between predicted and measured signal intensity.

Figure 14:
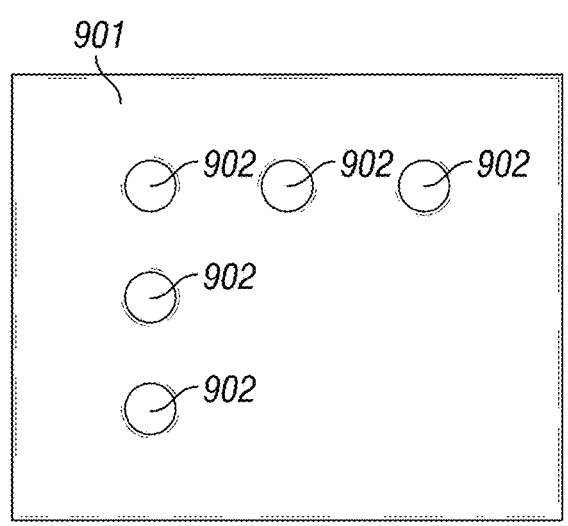
FIG. 14 shows a sample object with five voids that was used during testing.

Using a 225 kVp 2.3 mm Fe 1.0 mm Cu filtered X-ray spectra and a voxel pitch of 5.0 mm, 3D reconstructions of 2.0 cm diameter cylindrical void patterns in 0.7 g/cc wood crossties were generated. Using two orthogonally directed offset fan beams, 3D reconstructions were generated using only two transmission perspectives and a combination of all transmission and scatter perspectives. FIG. 14 shows a five void cylindrical void pattern 902 within a crosstie 901 that was used in testing.

Figure 15:
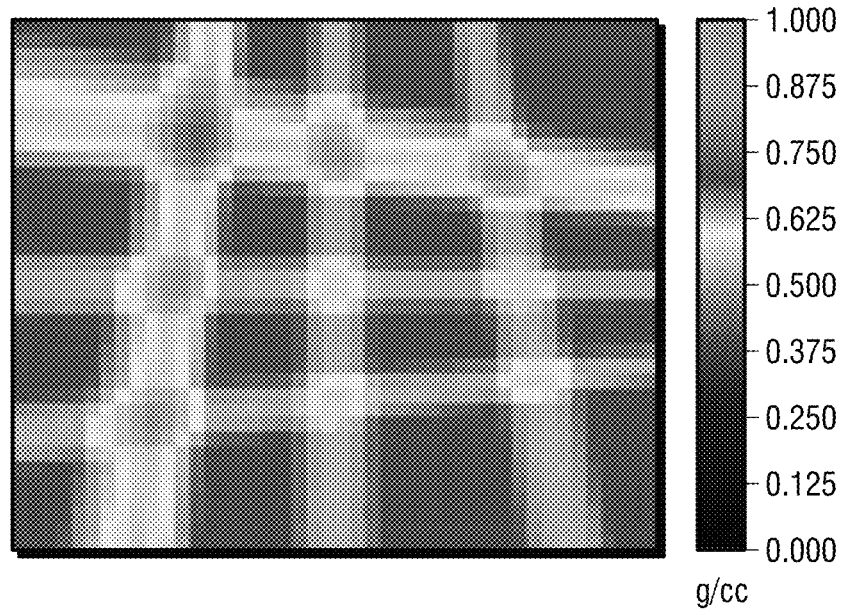
FIG. 15 shows a reconstruction of the sample object of FIG. 14 made of only two transmission radiography perspectives.
Figure 16:
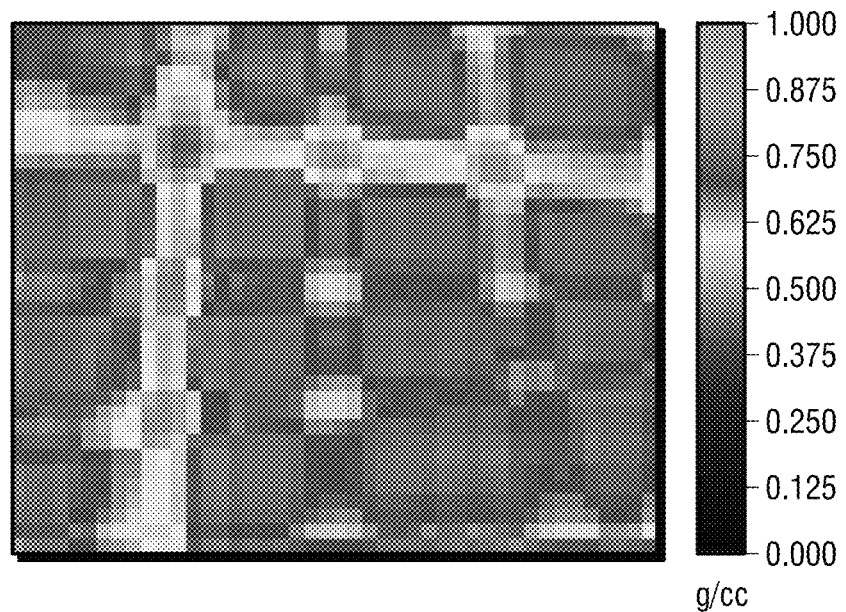
FIG. 16 shows a reconstruction of the sample object of FIG. 14 made of two transmission radiography perspectives and eight scatter radiography perspectives.

FIG. 15 shows a reconstruction of crosstie 901 and voids 902 made of only two transmission radiography perspectives. FIG. 16 shows a reconstruction of crosstie 901 and voids 902 made of two transmission radiography perspectives and eight scatter radiography perspectives. As may be seen in FIG. 16, the addition of scatter radiography perspectives adds information to the reconstruction and can reduce the influence of transmission radiography artifacts.

As demonstrated, with a limited number of transmission perspectives the accuracy of a reconstruction can be improved by using Compton scattered X-rays. This system and method would allow for wood to translate through a scanner at higher speeds than known systems because the X-ray sources and detectors would not move or rotate. An object could translate through this type of scanner at speeds exceeding 25 mph.

Although this disclosure has been described in terms of certain preferred embodiments, other embodiments that are apparent to those of ordinary skill in the art, including embodiments that do not provide all of the features and advantages set forth herein, are also within the scope of this disclosure. Accordingly, the scope of the present disclosure is defined only by reference to the appended claims and equivalents thereof.

What is claimed is:

1. A penetrating radiation inspection system comprising:
   at least one internal scanning subsystem having:
      a radiation source configured to produce a beam of radiation, the beam having a plurality of rays, the radiation source positioned to direct the beam of radiation into an object for internal inspection during relative translational motion between the at least one internal scanning subsystem and the object; and
      at least one detector positioned to at least partially measure an attenuated portion of the beam of radiation; and
   a processor configured to convert an estimated density of a portion of the object to a corrected estimated density by:
      determining a predicted attenuated portion using a density estimate;
      comparing the predicted attenuated portion to the measured attenuated portion to determine a signal difference;
      adjusting the density estimate of the portion of the object by scaling the density estimate using signal differences of rays that intersect the portion of the object; and
      repeatedly adjusting the density estimate until a difference between consecutive density estimates is below a selected threshold or a predetermined number of adjustments have been completed.

2. The system of claim 1, wherein the system is stationary and further comprises a travel path through the system, wherein the object is translated through the system on the travel path.

3. The system of claim 1, further comprising a surface scanning subsystem configured to scan a surface of the object to produce a three-dimensional surface profile of the object, wherein the processor is configured to approximate a boundary of the object using the three-dimensional surface profile and initially estimate the density of a plurality of portions of the object within the boundary.

4. The system of claim 1, wherein the at least one internal scanning subsystem is configured to measure the attenuated portion of the beam of radiation without rotating around the object.

5. The system of claim 1, wherein the at least one internal scanning subsystem is a plurality of internal scanning subsystems, at least two of the internal scanning subsystems being oriented in different perspectives.

6. The system of claim 5, wherein the at least two of the internal scanning subsystems are offset.

7. The system of claim 1, wherein the beam of radiation comprises a plurality of energies.

8. The system of claim 1, wherein the beam of radiation is a collimated fan beam, a collimated cone beam, or a collimated pencil beam.

9. The system of claim 1, wherein the at least one detector is configured to integrate the energy of all of the measured attenuated portions of the beam of radiation.

10. The system of claim 1, wherein the at least one detector is configured to determine energy levels of the measured attenuated portion of the beam of radiation.

11. The system of claim 1, wherein the at least one detector is at least one transmission detector, the attenuated portion of the beam is a transmitted portion of the beam, and the predicted attenuated portion of the beam is a predicted transmitted portion of the beam.

12. The system of claim 1, wherein the at least one detector is at least one scatter detector, the attenuated portion of the beam is a scattered portion of the beam, and the predicted attenuated portion of the beam is a predicted scattered portion of the beam.

13. The system of claim 12, further comprising collimators associated with the at least one scatter detector, the collimators being configured to limit detection of scattered portions of the beam of radiation to a field of view.

14. The system of claim 1, wherein the at least one detector includes at least one scatter detector and at least one transmission detector, the attenuated portion of the beam includes a scattered portion of the beam and a transmitted portion of the beam, and the predicted attenuated portion of the beam includes a predicted scattered portion of the beam and a predicted transmitted portion of the beam.

15. The system of claim 14, further comprising a filter associated with at least one of the at least one scatter detector and at least one transmission detector, the filter being configured to filter lower energy photons.

16. The system of claim 1, wherein the radiation source is an X-ray, a gamma ray source, or a combination thereof.

17. A method for three-dimensional image reconstruction comprising:
    translating at least one of an object and a radiation source;
    irradiating the object with a beam of radiation from a radiation source, the beam having a plurality of rays;
    measuring an attenuated portion of the beam with a first detector in a first perspective;
    converting an estimated density of a plurality of portions of the object to a corrected estimated density of each portion of the object using a computer system by:
        determining a predicted attenuated portion of the beam in the first perspective using a density estimate;
        comparing the predicted attenuated portion in the first perspective to the measured attenuated portion in the first perspective to determine a signal difference of each ray in the first perspective;
        adjusting the density estimate of the portion of the object by scaling the density estimate using signal differences of rays that intersect the portion of the object; and
        repeatedly adjusting the density estimate until a difference between consecutive density estimates is below a selected threshold or a predetermined number of adjustments have been completed; and
    generating a three-dimensional density array representing the object using the corrected estimated densities of the portions of the object.

18. The method of claim 17, wherein the attenuated portion of the beam is a scattered portion of the beam, the first detector is a scatter detector, and the predicted attenuated portion of the beam is a predicted scattered portion of the beam.

19. The method of claim 18, wherein the scatter detector has a plurality of detector elements, each detector element having a field of view, and the rays that intersect the portion of the object are rays that intersect the portion of the object and are within an intersecting field of view of the detector elements.

20. The method of claim 17, wherein the attenuated portion of the beam is a transmitted portion of the beam, the first detector is a transmission detector, and the predicted attenuated portion of the beam is a predicted transmitted portion of the beam.

21. The method of claim 17, further comprising:
    irradiating the object with a second beam of radiation from a second radiation source, the second beam having a plurality of rays;
    measuring an attenuated portion of the second beam with a second detector in a second perspective;
    determining a predicted attenuated portion of the second beam in the second perspective using a density estimate; and
    converting the estimated density of the plurality of portions of the object to a corrected estimated density of each portion of the object using an average signal difference of all the rays in the first and second perspectives that intersect the portion of the object.

22. The method of claim 21, wherein the attenuated portion of the beam is a transmitted portion of the second beam, the first detector is a transmission detector, and the predicted attenuated portion of the beam is a predicted transmitted portion of the beam.

23. The method of claim 22, wherein the attenuated portion of the second beam is a scattered portion of the second beam, the first detector is a scatter detector, and the predicted attenuated portion of the second beam is a predicted scattered portion of the second beam.

24. The method of claim 23, wherein the beam and the second beam are one beam.

25. The method of claim 21, wherein the second perspective is offset from the first perspective.

26. The method of claim 21, wherein the radiation source and the second radiation source are one radiation source.

27. The method of claim 17, wherein the beam of radiation from the radiation source has a plurality of energies.

28. The method of claim 17, further comprising:
    approximating a boundary of the object using a three-dimensional surface scan; and
    initially estimating a density of the portions of the object within the boundary.

29. The method of claim 17, wherein the radiation source does not rotate around the object.

30. A method for three-dimensional image reconstruction comprising:
    obtaining a measured attenuated portion of each of at least one beam of radiation, the at least one beam having a plurality of rays, the at least one beam of radiation being from a radiation source and having been attenuated by interaction with an object;
    converting an estimated density of a plurality of portions of the object to a corrected estimated density of each portion of the object using a computer system by:
        determining a predicted attenuated portion of the at least one beam using a density estimate;

comparing the predicted attenuated portion to the measured attenuated portion to determine a signal difference;

adjusting the density estimate of the portion of the object by scaling the density estimate using signal differences of rays that intersect the portion of the object; and repeatedly adjusting the density estimate until a difference between consecutive density estimates is below a selected threshold or a predetermined number of adjustments have been completed; and generating a three-dimensional density array representing the object using the corrected estimated densities of the portions of the object.

31. The method of claim 30, wherein the at least one beam of radiation is a plurality of beams of radiation oriented in different perspectives.

32. The method of claim 30, wherein:

the measured attenuated portion of each of at least one beam of radiation comprises a measured transmitted portion of a first beam of the at least one beam and a measured scattered portion of a second beam of the at least one beam;

determining a predicted attenuated portion of the at least one beam using the density estimate comprises determining a predicted transmitted portion of the first beam using a density estimate and determining a predicted scattered portion of the second beam using a density estimate;

the signal difference includes a transmitted signal difference and a scattered signal difference; and comparing the predicted attenuated portion to the measured attenuated portion to determine a signal difference comprises comparing the predicted transmitted portion to the measured transmitted portion to determine a transmitted signal difference and comparing the predicted scattered portion to the measured scattered portion to determine a scattered signal difference.

33. The method of claim 32, wherein adjusting the density estimate of the portion of the object by scaling the density estimate using signal differences of rays that intersect the portion of the object comprises adjusting the density estimate of the portion of the object by scaling the density estimate using transmitted signal differences of rays that intersect the portion of the object.

34. The method of claim 32, wherein adjusting the density estimate of the portion of the object by scaling the density estimate using signal differences of rays that intersect the portion of the object comprises adjusting the density estimate of the portion of the object by scaling the density estimate using scattered signal differences of rays that intersect the portion of the object.

35. The method of claim 32, wherein adjusting the density estimate of the portion of the object by scaling the density estimate using signal differences of rays that intersect the portion of the object comprises:

making an adjustment of the density estimate of the portion of the object by scaling the density estimate using scattered signal differences of rays that intersect the portion of the object; and making another adjustment of the density estimate of the portion of the object by scaling the density estimate using transmitted signal differences of rays that intersect the portion of the object.

36. The method of claim 32, wherein the first beam and the second beam are one beam.

37. The method of claim 32, wherein the first beam and the second beam are oriented in different perspectives.

38. The method of claim 30, wherein the measured attenuated portion is a measured transmitted portion and the predicted attenuated portion is a predicted transmitted portion.

39. The method of claim 30, wherein the measured attenuated portion is a measured scattered portion and the predicted attenuated portion is a predicted scattered portion.

40. The method of claim 30, wherein the at least one beam of radiation from the radiation source has a plurality of energies.

41. The method of claim 30, further comprising:

approximating a boundary of the object using a three-dimensional surface scan; and initially estimating the density of the portions of the object within the boundary.

42. A method for three-dimensional image reconstruction comprising:

obtaining a measured attenuated portion of a beam of radiation, the beam having been attenuated by interaction with an object;

determining a predicted attenuated portion of the beam of radiation using a density estimate;

iteratively adjusting the density estimate of the object by comparing the predicted attenuated portion and the measured attenuated portion, wherein the predicted attenuated portion is re-determined once the density estimate is adjusted; and generating a three-dimensional density array representing the object using the adjusted density estimate.

43. The method of claim 42, wherein the density estimate is iteratively updated until a difference between consecutive density estimates is below a selected threshold.

44. The method of claim 42, wherein the measured attenuated portion of the beam includes a measured scattered portion and a measured transmitted portion, and the predicted attenuated portion of the beam includes a predicted scattered portion and a predicted transmitted portion.

* * * * *